United States Patent
Maeda et al.

(10) Patent No.: US 9,108,986 B2
(45) Date of Patent: Aug. 18, 2015

(54) METHOD FOR PRODUCING OPTICALLY ACTIVE TETRAHYDROQUINOLINES

(75) Inventors: Sadayuki Maeda, Kyoto (JP); Tatsunori Sato, Hyogo (JP); Yasuhiko Kawano, Osaka (JP); Toshio Miyawaki, Hyogo (JP)

(73) Assignee: HAMARI CHEMICALS, LTD., Osaka (JP)

( * ) Notice: Subject to any disclaimer, the term of this patent is extended or adjusted under 35 U.S.C. 154(b) by 0 days.

(21) Appl. No.: 14/232,589

(22) PCT Filed: Jul. 13, 2012

(86) PCT No.: PCT/JP2012/067879
§ 371 (c)(1),
(2), (4) Date: Apr. 11, 2014

(87) PCT Pub. No.: WO2013/011930
PCT Pub. Date: Jan. 24, 2013

(65) Prior Publication Data
US 2014/0228572 A1  Aug. 14, 2014

(30) Foreign Application Priority Data

Jul. 15, 2011  (JP) ................. 2011-157043
Dec. 1, 2011  (JP) ................. 2011-263182

(51) Int. Cl.
| | |
|---|---|
| C07D 215/00 | (2006.01) |
| C07F 5/00 | (2006.01) |
| C07D 215/04 | (2006.01) |
| C07B 53/00 | (2006.01) |
| C07F 17/02 | (2006.01) |
| C07D 215/06 | (2006.01) |
| C07D 215/18 | (2006.01) |
| C07D 215/20 | (2006.01) |
| C07D 215/22 | (2006.01) |
| C07D 215/227 | (2006.01) |
| C07D 215/14 | (2006.01) |

(52) U.S. Cl.
CPC . *C07F 5/00* (2013.01); *C07B 53/00* (2013.01); *C07D 215/04* (2013.01); *C07D 215/06* (2013.01); *C07D 215/14* (2013.01); *C07D 215/18* (2013.01); *C07D 215/20* (2013.01); *C07D 215/22* (2013.01); *C07D 215/227* (2013.01); *C07F 17/02* (2013.01)

(58) Field of Classification Search
CPC .................................................. C07D 215/04
USPC ........................................................ 546/152
See application file for complete search history.

(56) References Cited

U.S. PATENT DOCUMENTS 8,222,452 B2 * 7/2012 Maeda ............................ 564/86
2010/0160636 A1 6/2010 Maeda

FOREIGN PATENT DOCUMENTS

EP           2772476 A1   9/2014
WO   WO-2009005024 A1   1/2009

OTHER PUBLICATIONS

Wang et al., Chem.Rev. 2012, 112, 2557-2590.*
Nunez-Rico et al. Organometallics, 2010, 29, 6627-6631.*
International Search Report in corresponding PCT/JP2012/067879 dated Aug. 14, 2012.
Written Opinion in corresponding PCT/JP2012/067879 dated Aug. 14, 2012.
Li et al., "Air-Stable and Phosphine-Free Iridium Catalysts for Highly Enantioselective Hydrogenation of Quinoline Derivatives," *Organic Letters*, vol. 10, No. 22, pp. 5265-5268 (2008).
Wang et al., Highly Enantioselective Iridium-Catalyzed Hydrogenation of Heteroaromatic Compounds, Quinolines, *J. Am. Chem. Soc.*, vol. 125, pp. 10536-10537 (2003).
Reuping et al., "A Highly Enantioselective Bronsted Acid Catalyzed Cascade Reaction: Organocatalytic Transfer Hydrogenation of Quinolines and their Application in the Synthesis of Alkaloids," *Angew. Chem. Int. Ed.*, vol. 45, pp. 3683-3686 (2006).
Wang et al., "pH-Regulated Asymmetric Transfer Hydrogenation of Quinolines in Water**", *Angew. Chem. Int. Ed.*, vol. 48, pp. 6524-6528 (2009).
International Preliminary Report on Patentability in corresponding PCT/JP2012/067879 dated Jan. 21, 2014. (English Translation).
Hoffmuller et al., "Metallkomplexe mit biologisch wichtigen Liganden. XCV [1]", *Z. anorg. allg. Chem.* 623, pp. 1903-1911 (1997).
Extended European Search Report in PCT/JP2012/067879 dated Nov. 3, 2014.

* cited by examiner

*Primary Examiner* — Nizal Chandrakumar
(74) *Attorney, Agent, or Firm* — Marshall, Gerstein & Borun LLP

(57) ABSTRACT

Provided are a novel chiral iridium(III) complex; and a method for producing optically active 2-substituted-1,2,3,4-tetrahydroquinolines from 2-substituted-quinolines with the use of the chiral iridium(III) complex through a more economical and easy production process. The disclosed method for producing optically active 2-substituted-1,2,3,4-tetrahydroquinolines comprises reducing a quinoline compound represented by formula [I]:

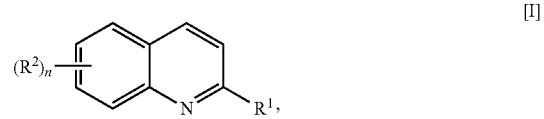

in the presence of a hydrogen donor compound and an iridium (III) complex having a chiral prolinamide compound as a ligand to give an optically active 2-substituted-1,2,3,4-tetrahydroquinoline represented by formula [II]:

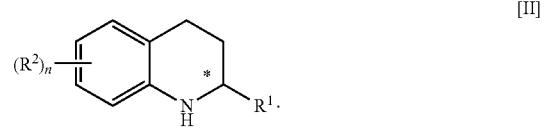

12 Claims, 2 Drawing Sheets

METHOD FOR PRODUCING OPTICALLY ACTIVE TETRAHYDROQUINOLINES

TECHNICAL FIELD

The present invention relates to a method for producing optically active 2-substituted-1,2,3,4-tetrahydroquinolines; and a novel chiral iridium catalyst used for the method.

BACKGROUND ART

Optically active tetrahydroquinolines, particularly the ones having a substituent at position 2, namely optically active 2-substituted-1,2,3,4-tetrahydroquinolines, are contained in many natural bioactive compounds such as alkaloids and are important compounds widely used as pharmaceuticals.

For efficient production of optically active 2-substituted tetrahydroquinolines, various methods involving asymmetric reduction of the corresponding 2-substituted-quinolines to give optically active 2-substituted-1,2,3,4-tetrahydroquinolines in one step have been developed. For example, known methods include a method using Hantzsch ester as a reducing agent and a chiral acid as an asymmetric catalyst (Non Patent Literature 1); a method using hydrogen gas as a reducing agent and an iridium catalyst having a chiral ligand (Non Patent Literature 2 and 3); and a method using sodium formate as a reducing agent, water as a solvent and a rhodium catalyst coordinated with TsDPEN or its related ligand (Non Patent Literature 4).

However, these methods are not necessarily satisfactory for industrial use. For example, the method using Hantzsch ester as a reducing agent (Non Patent Literature 1) requires a stoichiometric amount of very expensive Hantzsch ester and thus is difficult to apply to industrial production. The method using hydrogen gas as a reducing agent (Non Patent Literature 2 and 3) requires high-pressure conditions (for example, 40 to 50 atmospheres) for a reaction with hydrogen due to the low conversion of quinoline, and thus needs specialized equipment for large scale production, which leads to high production cost.

The method using inexpensive sodium formate as a reducing agent and water as a solvent (Non Patent Literature 4) is also industrially disadvantageous because of the following reasons: most of quinoline compounds as a starting material are poorly water-soluble; precise pH adjustment is indispensable; and rhodium complexes essential as a catalyst are expensive. In addition, a reaction of 2-methylquinoline using an iridium catalyst having a TsDPEN ligand (Non Patent Literature 4) has problems including the low enantiomeric excess of the product, which is as low as 11%.

Under such circumstances, there is a pressing need to develop methods for providing optically active 2-substituted-1,2,3,4-tetrahydroquinolines usable as a unit of many useful substances in an industrially advantageous manner.

CITATION LIST

Patent Literature

Patent Literature 1: WO 2009/005024

Non Patent Literature

Non Patent Literature 1:
Angew. Chem. Int. Ed, 2006, 45, 3683-3686
Non Patent Literature 2:
J. Am. Chem. Soc, 2003, 125, 10536-10537
Non Patent Literature 3:
Org. Lett, 2008, 10, 5265-5268
Non Patent Literature 4:
Angew. Chem. Int. Ed, 2009, 48, 6524-6528

SUMMARY OF INVENTION

Technical Problem

An object of the present invention is to provide a novel chiral iridium(III) complex; and a method for producing optically active 2-substituted-1,2,3,4-tetrahydroquinolines from 2-substituted-quinolines with the use of the chiral iridium(III) complex through a more economical and easy production process.

Solution to Problem

The present inventors already filed a patent application claiming a method for producing optically active amines from imine compounds formed of ketone and amine, comprising preparing in situ an iridium(III) complex catalyst having a chiral prolinamide compound as a ligand, and using the resulting catalyst-containing mixture as it is for asymmetric transfer hydrogenation of an imine compound in the presence of a hydrogen donor compound (Patent Literature 1). It was newly found that, by use of this method for asymmetric reduction of 2-substituted-quinolines, optically active 2-substituted-1,2,3,4-tetrahydroquinolines can be produced with fairly high conversion and enantioselectivity. In addition, in the case where an isolated and purified crystalline iridium(III) complex having a chiral prolinamide compound as a ligand is used as a catalyst for the asymmetric reduction of 2-substituted-quinolines, optically active 2-substituted-1,2,3,4-tetrahydroquinolines can be obtained with a further higher chemical yield and enantiomeric excess. The present inventors further conducted a great deal of examination and then completed the present invention. That is, the present invention provides a method for producing optically active 2-substituted-1,2,3,4-tetrahydroquinolines by asymmetric reduction of 2-substituted-quinolines in an industrially advantageous manner.

That is, the present invention includes the following.

[1] A method for producing optically active 2-substituted-1,2,3,4-tetrahydroquinolines, comprising reducing a quinoline compound represented by formula [I]:

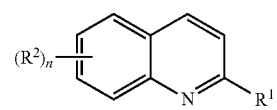

(wherein $R^1$ represents an optionally substituted alkyl group, an optionally substituted aryl group, an optionally substituted aralkyl group, an optionally substituted cycloalkyl group or an optionally substituted heteroaryl group, $R^2$ represents a hydrogen atom, an optionally substituted alkyl group, an optionally substituted aryl group, an optionally substituted aralkyl group, an optionally substituted cycloalkyl group, an optionally substituted heteroaryl group, an optionally substituted hydroxyl group, an optionally substituted thiol group, an optionally substituted amino group, an optionally substituted carbamoyl group, an optionally substituted aryloxy group, an optionally substituted heteroaryloxy group, a carboxyl group, an esterified carboxyl group, a cyano group, a nitro group or a halogen atom, $R^2$ is bound to the quinoline ring at any one of positions 5 to 8, n is an integer of 1 to 4, and when n is not less than 2, $R^2$ groups adjacent to each other may join together to form a ring), in the presence of a hydrogen donor compound and an iridium (III) complex having a chiral prolinamide compound as a ligand to give an optically active 2-substituted-1,2,3,4-tetrahydroquinoline represented by formula [II]:

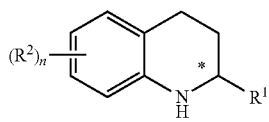

(wherein $R^1$, $R^2$ and n are as defined in formula [I], and the symbol "*" indicates that the carbon atom is a chiral center).

[2] The method according to the above [1], wherein the chiral prolinamide compound is a compound represented by formula [III]:

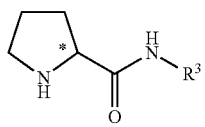

(wherein $R^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center).

[3] The method according to the above [1] or [2], wherein the chiral prolinamide compound is (R)-proline heteroaryl amide or (S)-proline heteroaryl amide.

[4] The method according to any one of the above [1] to [3], wherein the chiral prolinamide compound is (R)—N-(6-quinolinyl)-2-pyrrolidinecarboxamide or (S)—N-(6-quinolinyl)-2-pyrrolidinecarboxamide.

[5] The method according to any one of the above [1] to [3], wherein the chiral prolinamide compound is (R)—N-(2-methoxy-3-dibenzofuranyl)-2-pyrrolidinecarboxamide or (S)—N-(2-methoxy-3-dibenzofuranyl)-2-pyrrolidinecarboxamide.

[6] The method according to the above [1] or [2], wherein the chiral prolinamide compound is (R)-2-pyrrolidinecarboxamide or (S)-2-pyrrolidinecarboxamide.

[7] The method according to any one of the above [1] to [3], wherein the iridium(III) complex having a chiral prolinamide compound as a ligand is represented by formula [IV]:

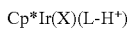

(wherein X represents Cl⁻, p-CH₃C₆H₄SO₃⁻, CH₃SO₃⁻, CF₃SO₃⁻, NO₃⁻, BF₄⁻, ClO₄⁻, PF₆⁻, SbF₆⁻, B[3,5-di(trifluoromethyl)phenyl]₄⁻ or B(4-fluorophenyl)₄⁻, L is a compound represented by formula [III]:

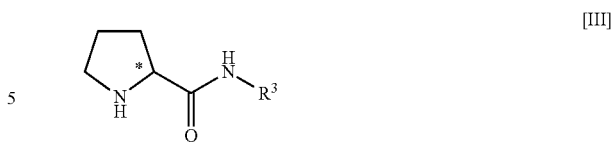

(wherein $R^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center), and Cp* represents (1,2,3,4,5-η)-pentamethyl-2,4-cyclopentadien-1-yl).

[8] The method according to the above [7], wherein the complex has a ligand of formula [III] in which $R^3$ is hydrogen, a 6-quinolinyl group or a 2-methoxy-3-dibenzofuranyl group.

[9] The method according to the above [7] or [8], wherein the iridium(III) complex having a chiral prolinamide compound as a ligand is an (R)- or (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) catalyst, or an (R)- or (S)-chloro[(1,2,3,4,5-η)-pentamethyl-2,4-cyclopentadien-1-yl](N-6-quinolinyl-2-pyrrolidinecarboxamidato-κN1, κN2)iridium(III) catalyst.

[10] The method according to the above [7] or [8], wherein the iridium(III) complex having a chiral prolinamide compound as a ligand is an (R)- or (S)-chloro[(1,2,3,4,5-η)-pentamethyl-2,4-cyclopentadien-1-yl](2-pyrrolidinecarboxamidato-κN1, κN2)iridium(III) catalyst.

[11] The method according to any one of the above [1] to [10], wherein the iridium(III) complex having a chiral prolinamide compound as a ligand is crystalline.

[12] The method according to any one of the above [1] to [10], wherein the iridium(III) complex having a chiral prolinamide compound as a ligand is amorphous.

[13] The method according to any one of the above [1] to [12], wherein the hydrogen donor compound is formic acid.

[14] An iridium(III) complex represented by formula [IV]:

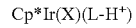

(wherein X represents Cl⁻, p-CH₃C₆H₄SO₃⁻, CH₃SO₃⁻, CF₃SO₃⁻, NO₃⁻, BF₄⁻, ClO₄⁻, PF₆⁻, SbF₆⁻, B[3,5-di(trifluoromethyl)phenyl]₄⁻ or B(4-fluorophenyl)₄⁻, L is a compound represented by formula [III]:

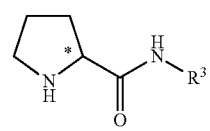

(wherein $R^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center), and Cp* represents (1,2,3,4,5-η)-pentamethyl-2,4-cyclopentadien-1-yl).

[15] The iridium(III) complex according to the above [14], having a ligand of formula [III] in which $R^3$ is hydrogen, a 6-quinolinyl group or a 2-methoxy-3-dibenzofuranyl group.

[16] An (R)- or (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) complex.

[17] An (R)- or (S)-chloro[(1,2,3,4,5-η)-pentamethyl-2,4-cyclopentadien-1-yl][N-6-quinolinyl-2-pyrrolidinecarboxamidato-κN1, κN2)iridium(III) complex.

[18] An (R)- or (S)-chloro[(1,2,3,4,5-η)-pentamethyl-2,4-cyclopentadien-1-yl](2-pyrrolidinecarboxamidato-κN1, κN2)iridium(III) complex.

[19] The iridium(III) complex according to any one of the above [14] to [18], which is crystalline.

[20] The iridium(III) complex according to any one of the above [14] to [18], which is amorphous.

[21] A method for producing the iridium(III) chloro complex according to any one of the above [14] to [20], comprising bringing a chiral prolinamide compound into contact with a pentamethylcyclopentadienyl iridium(III) chloride dimer in the presence of a weak base.

[22] The method according to the above [21], wherein the weak base is a tertiary amine, an alkali metal hydrogen carbonate or an alkali earth metal carbonate.

Advantageous Effects of Invention

The production method of the present invention enables low-cost and industrially advantageous production of optically active 2-substituted-1,2,3,4-tetrahydroquinolines using general-purpose equipment under simple process control.

DESCRIPTION OF EMBODIMENTS

Figure 1:
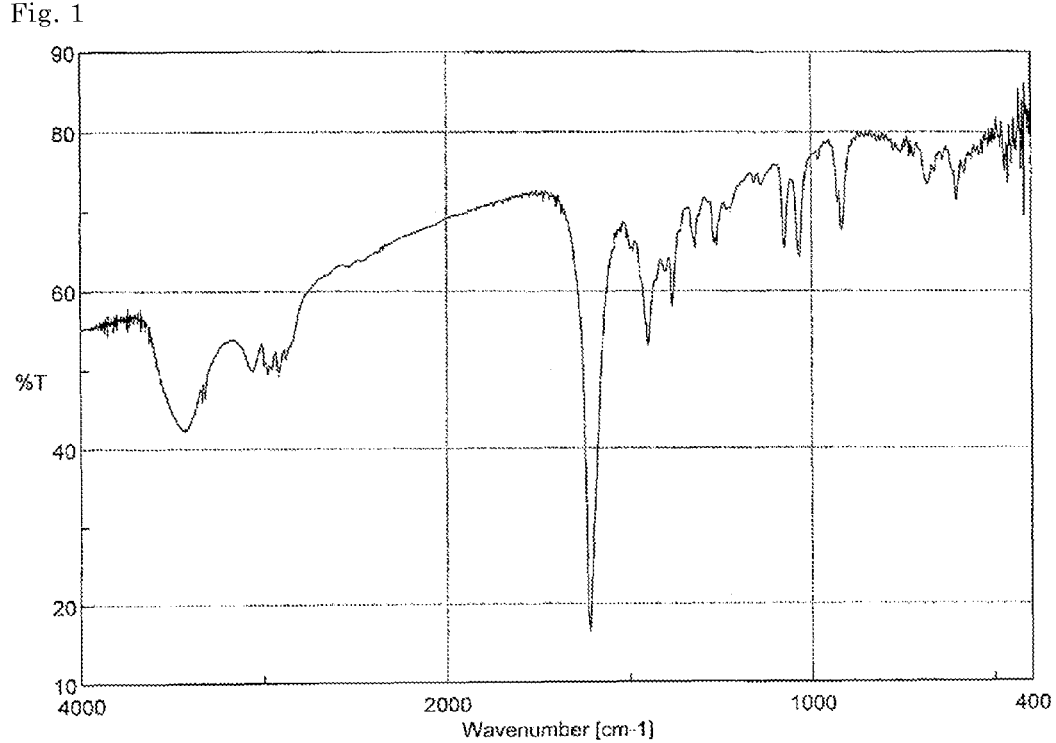
FIG. 1 shows an IR (KBr) chart of the crystalline (S)-chloro[(1,2,3,4,5-η)-pentamethyl-2,4-cyclopentadien-1-yl](2-pyrrolidinecarboxamidato-κN1, κN2)iridium(III) produced in Example 4.

Preparation of Iridium(III) Complex Having a Chiral Prolinamide Compound as a Ligand An iridium(III) chloro complex having a chiral prolinamide compound as a ligand can be prepared by, for example, allowing a reaction of an iridium(III) compound with a chiral prolinamide compound and a base. Complexes other than the iridium(III) chloro complex, that is, iridium(III) complexes having a p-CH$_3$C$_6$H$_4$SO$_3^-$, CH$_3$SO$_3^-$, CF$_3$SO$_3^-$, NO$_3^-$, BF$_4^-$, ClO$_4^-$, PF$_6^-$, SbF$_6^-$, B[3,5-di(trifluoromethyl)phenyl]$_4^-$ or B(4-fluorophenyl)$_4^-$ anion can be prepared from, for example, the iridium (III) chloro complex having a chiral prolinamide compound as a ligand.

The iridium(III) complex having a chiral prolinamide compound as a ligand is a complex formed of a chiral prolinamide compound represented by formula [III]:

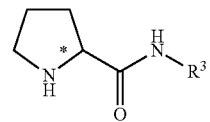

[III]

(wherein R$^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center) and
a trivalent iridium compound, and hereinafter also called an iridium(III) complex.

The iridium(III) complex having a chiral prolinamide compound as a ligand can be generally represented by the following formula:

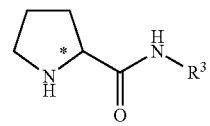

(wherein R$^3$ and * are as defined in the previously described formula [III]).

Herein, the iridium(III) complex having a chiral prolinamide compound as a ligand is represented by formula [IV]:

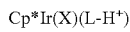

Cp*Ir(X)(L-H$^+$)  [IV]

(wherein X represents Cl$^-$, p-CH$_3$C$_6$H$_4$SO$_3^-$, CH$_3$SO$_3^-$, CF$_3$SO$_3^-$, NO$_3^-$, BF$_4^-$, ClO$_4^-$, PF$_6^-$, SbF$_6^-$, B[3,5-di(trifluoromethyl)phenyl]$_4^-$ or B(4-fluorophenyl)$_4^-$, L is a compound represented by formula [III]:

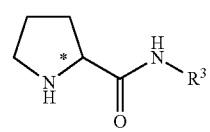

[III]

(wherein R$^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center), and Cp* represents (1,2,3,4,5-η)-pentamethyl-2,4-cyclopentadien-1-yl).

Preferably, the iridium(III) complex having a chiral prolinamide compound as a ligand has a ligand of formula [III] in which R$^3$ is hydrogen, a 6-quinolinyl group or a 2-methoxy-3-dibenzofuranyl group.

Herein, it is also possible that the iridium(III) complex represented by formula [IV] is represented by formula [VI]:

[Cp*Ir(L-H$^+$)]$^+$(X)  [VI]

(wherein each symbol is as defined in formula [IV]).

In formula [IV], exemplary prolinamide compounds include 2-pyrrolidinecarboxamide, exemplary prolinamide quinoline derivatives include N-6-quinolinyl-2-pyrrolidinecarboxamide, and exemplary prolinamide methoxy dibenzofuran derivatives include N-(2-methoxy-3-dibenzofuranyl)-2-pyrrolidinecarboxamide.

Specific examples of the iridium(III) complex having a chiral prolinamide compound as a ligand include an (R)- or (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) complex, an (R)- or (S)-chloro [(1,2,3,4,5-η)-pentamethyl-2,4-cyclopentadien-1-yl](N-6-quinolinyl-2-pyrrolidinecarboxamidato-κN1, κN2)iridium (III) complex, and an (R)- or (S)-chloro[(1,2,3,4,5-η)-pentamethyl-2,4-cyclopentadien-1-yl](2-pyrrolidinecarboxamidato-κN1, κN2)iridium(III) complex.

The compounds described herein can be expressed in another notation as shown in Table 1 and both expressions are interchangeable. The same holds true for the case where the ligand shown in Table 1 is replaced with a ligand other than Cl$^-$, such as p-CH$_3$C$_6$H$_4$SO$_3^-$, CH$_3$SO$_3^-$, CF$_3$SO$_3^-$, NO$_3^-$, BF$_4^-$, ClO$_4^-$, PF$_6^-$, SbF$_6^-$, B[3,5-di(trifluoromethyl)phenyl]$_4^-$ or B(4-fluorophenyl)$_4^-$. For example, Cp*Ir(PF$_6^-$)(R-PMDBFA-H$^+$) and (R)-hexafluorophosphate[(1,2,3,4,5-η)-pentamethyl-2,4-cyclo pentadien-1-yl][N-(2-methoxy-3-dibenzofuranyl)-2-pyrrolidinecarboxamidato-κN1, κN2] iridium(III) are interchangeable.

TABLE 1

| Compound | Another notation |
| --- | --- |
| Cp*Ir (Cl$^-$) (R-PA-H$^+$) | (R)-chloro[(1,2,3,4,5-η)-pentamethyl-2,4-cyclopentadien-1-yl](2-pyrrolidinecarboxamidato-κN1, κN2)iridium(III) |
| Cp*Ir (Cl$^-$) (S-PA-H$^+$) | (S)-chloro[(1,2,3,4,5-η)-pentamethyl-2,4-cyclopentadien-1-yl](2-pyrrolidinecarboxamidato-κN1, κN2)iridium(III) |
| Cp*Ir (Cl$^-$) (R-PQA-H$^+$) | (R)-chloro[(1,2,3,4,5-η)-pentamethyl-2,4-cyclopentadien-1-yl](N-6-quinolinyl-2-pyrrolidinecarboxamidato-κN1, κN2)iridium(III) |
| Cp*Ir (Cl$^-$) (S-PQA-H$^+$) | (S)-chloro[(1,2,3,4,5-η)-pentamethy-2,4-cyclopentadien-1-y](N-6-quinolinyl-2-pyrrolidinecarboxamidato-κN1, κN2)iridium(III) |
| Cp*Ir (Cl$^-$) (R-PMDBFA-H$^+$) | (R)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) |
| Cp*Ir (Cl$^-$) (S-PMDBFA-H$^+$) | (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) |

The iridium(III) complex having a chiral prolinamide compound as a ligand may be crystalline or amorphous, but is preferably crystalline.

After the iridium(III) complex having a chiral prolinamide compound as a ligand is prepared, the resulting catalyst-containing mixture can be directly used as a catalyst for asymmetric reduction, but more preferably, an crystalline or amorphous iridium(III) complex isolated and purified from the catalyst-containing mixture is used for asymmetric reduction. This is because, when the isolated and purified iridium (III) complex in a crystalline or amorphous form is used as a catalyst for asymmetric reduction, the chemical yield and the enantiomeric excess of the product will be higher than those in the case where the catalyst-containing mixture is directly used.

The reason for this is that, during the preparation of the catalyst and the subsequent period when the resulting catalyst-containing mixture is left unused, the base in the catalyst-containing mixture causes partial epimerization of the iridium(III) complex, which results in a reduced optical purity of the catalyst. Therefore, in the case where the catalyst-containing mixture is directly used, it should be used immediately after the preparation. In contrast, in the case where the iridium(III) complex is isolated and purified from the catalyst-containing mixture, the base responsible for epimerization and the epimerized product (epimer) can be eliminated, and thus the iridium(III) complex can be obtained in a crystalline or amorphous form with high optical purity and good preservation stability.

Examples of the isolation and purification method include the following. In one example, the produced iridium(III) complex is isolated by, for example, concentration of the reaction mixture and subsequently purified by a known recrystallization or reprecipitation method. In another example, complex formation is performed in a solvent that allows highly efficient purification, and after a purification process, the resulting precipitate as the main product is collected by filtration, washed and dried. By use of any of these methods, the iridium(III) complex can be easily obtained in a crystalline or amorphous form as a chemically and optically pure product.

The isolated and purified iridium(III) complex in a crystalline or amorphous form is highly stable, the chemical purity and the optical purity thereof stay constant for a long period, and thus the complex can be preserved at room temperature for a long period. With the use of this complex as a catalyst for asymmetric reduction, the reduction product can be obtained with high chemical yield and enantiomeric excess.

The iridium(III) complex can be preferably used as a catalyst for asymmetric reduction in the production of, for example, optically active tetrahydroquinolines, optically active amines, etc.

The term "crystalline" as used herein generally means that molecules are regularly arranged in three dimensions. The term "amorphous" as used herein generally means that molecules form no space lattice and are randomly distributed.

<Iridium(III) Compound>

Examples of the iridium(III) compound used for the preparation of the iridium(III) chloro complex include a pentamethylcyclopentadienyl iridium(III) chloride dimer ([Cp*IrCl$_2$]$_2$), acetylacetonato iridium(III) and tris(norbornadiene)(acetylacetonato)iridium(III), and particularly preferred is a pentamethylcyclopentadienyl iridium(III) chloride dimer ([Cp*IrCl$_2$]$_2$). The iridium(III) chloro complex can be used for the preparation of other iridium(III) complexes, that is, iridium(III) complexes having a p-CH$_3$C$_6$H$_4$SO$_3^-$, CH$_3$SO$_3^-$, CF$_3$SO$_3^-$, NO$_3^-$, BF$_4^-$, ClO$_4^-$, PF$_6^-$, SbF$_6^-$, B[3,5-di(trifluoromethyl)phenyl]$_4^-$ or B(4-fluorophenyl)$_4^-$ anion.

<Chiral Prolinamide Compound>

Examples of the chiral prolinamide compound used for the preparation of the iridium(III) chloro complex include a compound represented by formula [III]:

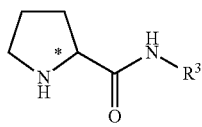

[III]

(wherein R³ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center).

Examples of the prolinamide compound represented by formula [III] include, in addition to prolinamide, N-substituted amide such as N-alkyl amide, N-cycloalkyl amide, N-aryl amide, N-heteroaryl amide, N-aralkyl amide and N-heteroaryl alkyl amide. These substituting groups are examples of R³ and may also have a substituting group (hereinafter also called a substituent).

The "alkyl" moiety in the N-alkyl amide is, for example, a straight or branched alkyl group having 1 to 20 carbon atoms but no chiral carbon atoms. The specific examples include methyl, ethyl, propyl, isopropyl, butyl, isobutyl, tert-butyl, pentyl, hexyl, heptyl, octyl, nonyl, decyl, dodecyl, pentadecyl, hexadecyl and octadecyl.

The "cycloalkyl" moiety in the N-cycloalkyl amide is, for example, a cycloalkyl group having 3 to 7 carbon atoms. The specific examples include cyclopropyl, cyclobutyl, cyclopentyl, cyclohexyl and cycloheptyl.

The "aryl" moiety in the N-aryl amide is, for example, an aryl group having 6 to 20 carbon atoms. The specific examples include phenyl, 1-naphthyl, 2-naphthyl, anthryl, phenanthryl, 2-biphenyl, 3-biphenyl, 4-biphenyl and terphenyl.

The "heteroaryl" moiety in the N-heteroaryl amide is, for example, a heteroaryl group having a heteroatom selected from a nitrogen atom, a sulfur atom, an oxygen atom and the like. The specific examples include furanyl, thienyl, oxazolyl, isoxazolyl, thiazolyl, isothiazolyl, pyrrolyl, imidazolyl, pyrazolyl, pyridyl, pyrimidinyl, pyrazinyl, phthalazinyl, triazinyl, indolyl, isoindolyl, quinolinyl, isoquinolinyl and dibenzofuranyl.

The "aralkyl" moiety in the N-aralkyl amide is, for example, a group which is the same as the above-defined alkyl group except for having an aryl group instead of a hydrogen atom. The specific examples include benzyl, phenylethyl and phenylpropyl.

The "heteroarylalkyl" moiety in the N-heteroaryl alkyl amide is, for example, a group which is the same as the above-defined alkyl group except for having a heteroaryl group instead of a hydrogen atom. The specific examples include heteroarylmethyl, heteroarylethyl and heteroarylpropyl.

The substituting group (substituent) in the above "alkyl", "aryl", "heteroaryl", "aralkyl" and "cycloalkyl" moieties may be of any kind unless the substituting group adversely affects the reaction, and the examples include halogens (for example, a fluorine, chlorine, bromine or iodine atom, etc.), straight or branched alkyl groups having 1 to 6 carbon atoms (for example, methyl, ethyl, propyl, isopropyl, butyl, isobutyl, tert-butyl, pentyl, hexyl, etc.), aralkyl groups having 7 to 12 carbon atoms (for example, phenylethyl, phenylpropyl, naphthylmethyl, etc.), straight or branched alkoxy groups having 1 to 6 carbon atoms (for example, methoxy, ethoxy, propoxy, isopropoxy, butoxy, isobutoxy, tert-butoxy, pentyloxy, etc.), alkyl halide groups (for example, monofluoromethyl, difluoromethyl, trifluoromethyl, difluoroethyl, trifluoroethyl, trichloromethyl, etc.), alkoxy halide groups (for example, fluoromethoxy, difluoromethoxy, trifluoromethoxy, trifluoroethoxy, tetrafluoroethoxy, etc.), a hydroxyl group, a mercapto group, a nitro group, a nitrile group, a carboxyl group and an alkoxycarbonyl group. Hereinafter, the substituting group (substituent) of this kind is called substituting group (A) in some cases.

The chiral prolinamide compound is preferably (R)- or (S)-prolinamide or (R)- or (S)-proline heteroaryl amide, and more preferably (R)— or (S)-proline heteroaryl amide. A preferable chiral proline heteroaryl amide compound is (R)— or (S)—N-(6-quinolinyl)-2-pyrrolidinecarboxamide, (R)— or (S)—N-(2-methoxy-3-dibenzofuranyl)-2-pyrrolidinecarboxamide or the like because the use of these compounds as a ligand of the iridium(III) complex catalyst for a reducing reaction is advantageous in terms of the degree of conversion and the optical purity of the product.

These chiral prolinamide compounds can be used for not only the iridium(III) chloro complex but also other iridium (III) complexes, that is, iridium(III) complexes having a p-$CH_3C_6H_4SO_3^-$, $CH_3SO_3^-$, $CF_3SO_3^-$, $NO_3^-$, $BF_4^-$, $ClO_4^-$, $PF_6^-$, $SbF_6^-$, $B[3,5-di(trifluoromethyl)phenyl]_4^-$ or $B(4-fluorophenyl)_4^-$ anion.

The amount of the chiral prolinamide compound used for the complex preparation is usually about 0.1 to 10 mol, and preferably about 0.5 to 4 mol per mole of the iridium(III) compound as a starting material.

In the case where the iridium(III) compound is a dimer, the amount of the chiral prolinamide compound used for the complex preparation is usually about 2 to 3 mol, and preferably about 2 to 2.2 mol per mole of the dimer.

<Base>

The base used for the preparation of the iridium (III) chloro complex is preferably a weak base, and is more preferably a tertiary amine, an alkali metal hydrogen carbonate or an alkali earth metal carbonate. Preferable examples of the weak base include tertiary amines such as triethylamine, trimethylamine, tributylamine and N-methylmorpholine; alkali metal hydrogen carbonates such as sodium hydrogen carbonate and potassium hydrogen carbonate; and alkali earth metal carbonates such as calcium carbonate and magnesium carbonate, and particularly preferred is triethylamine. Strong bases including alkali metal hydroxides, such as sodium hydroxide and potassium hydroxide, and sodium methoxide, are not preferable for use in the catalyst preparation because strong bases accelerate the epimerization of the produced prolinamide complex, which reduces the optical purity of the product.

In the case where the iridium(III) compound as a starting material is a dimer, the amount of the base used for the complex preparation is usually about 2 to 3 mol, and preferably about 2 to 2.2 mol per mole of the dimer.

<Reaction>

The iridium(III) chloro complex having a chiral prolinamide compound as a ligand can be prepared by, for example, adding an iridium(III) compound and a base to a chiral prolinamide compound preferably dissolved in a solvent, and preferably stirring the mixture.

The reaction temperature in the present invention is not particularly limited, but is usually −30 to 200° C., preferably −10 to 100° C., more preferably 5 to 40° C., and particularly preferably room temperature.

The reaction time in the present invention is not particularly limited, but is usually 1 minute to 72 hours, preferably 3 minutes to 48 hours, and particularly preferably 10 minutes to 20 hours.

After the completion of the reaction, the desired optically active tetrahydroquinoline can be obtained by known treatments such as concentration, extraction, filtration and washing. If needed, crystallization, recrystallization, salt formation with an achiral acid such as hydrochloric acid, sulfuric acid, methanesulfonic acid, formic acid and trifluoroacetic acid, followed by recrystallization, and chemical optical resolution using chiral mandelic, tartaric, dibenzoyltartaric, ditoluoyl tartaric, 10-camphor sulfonic or malic acid may be employed to obtain the optically active tetrahydroquinoline in a higher optical purity.

In the preparation of the iridium(III) chloro complex having a chiral prolinamide compound as a ligand, it is preferable that a chiral prolinamide compound is brought into contact with a pentamethylcyclopentadienyl iridium(III) chloride dimer in the presence of a weak base.

<Metal Salt>

In the preparation of iridium(III) complexes other than the iridium(III) chloro complex, that is, iridium(III) complexes having a p-$CH_3C_6H_4SO_3^-$, $CH_3SO_3^-$, $CF_3SO_3^-$, $NO_3^-$, $BF_4^-$, $ClO_4^-$, $PF_6^-$, $SbF_6^-$, B[3,5-di(trifluoromethyl)phenyl]$_4^-$ or B(4-fluorophenyl)$_4^-$ anion, it is preferable to additionally use a metal salt represented by formula [V]:

$$M_a X_b \qquad [V]$$

(wherein M represents a mono- to trivalent metal cation, X represents p-$CH_3C_6H_4SO_3^-$, $CH_3SO_3^-$, $CF_3SO_3^-$, $NO_3^-$, $BF_4^-$, $ClO_4^-$, $PF_6^-$, $SbF_6^-$, B[3,5-di(trifluoromethyl)phenyl]$_4^-$ or B(4-fluorophenyl)$_4^-$, a represents an integer of 1 to 3, and b represents an integer of 1 to 3).

The addition of this metal salt allows the replacement of the chloro anion in the iridium(III) chloro complex with the anion represented by X in the metal salt, resulting in the production of iridium(III) complexes containing the desired anion.

M is, for example, a monovalent metal cation such as a lithium ion, a sodium ion, a potassium ion, a copper(I) ion, a mercury(I) ion, a silver ion, etc.; a divalent metal cation such as a magnesium ion, a calcium ion, a strontium ion, a barium ion, a cadmium ion, a nickel(II) ion, a zinc ion, a copper(II) ion, a mercury(II) ion, a cobalt(II) ion, a tin(II) ion, a lead(II) ion, a manganese(II) ion, etc.; and a trivalent metal cation such as an aluminum ion, an iron(III) ion, a chromium(III) ion, etc. Preferred is a monovalent metal cation and more preferred is a silver ion.

Examples of the metal salt represented by formula [V] include silver hexafluorophosphate, silver trifluoromethanesulfonate, silver hexafluoroantimonate, silver perchlorate and silver tetrafluoroborate.

The amount of the metal salt used for the complex preparation is, for example, usually about 0.7 to 1.4 mol, and preferably about 0.9 to 1.1 mol per mole of the iridium (III) chloro complex.

<Solvent>

In the preparation of the iridium(III) complex, it is preferable to use a solvent. The solvent is not particularly limited and may be an inorganic or organic solvent, but preferred is an organic solvent.

Examples of the organic solvent include aliphatic hydrocarbons (for example, pentane, hexane, heptane, octane, cyclohexane, etc.); aromatic hydrocarbons (for example, benzene, toluene, xylene, etc.); halogenated hydrocarbons (for example, dichloromethane, 1,2-dichloroethane, chloroform, carbon tetrachloride, o-dichlorobenzene, etc.); alcohols (for example, methanol, ethanol, isopropyl alcohol, tert-butyl alcohol, tert-amyl alcohol, etc.); ethers (for example, dimethyl ether, ethylmethyl ether, diethyl ether, diisopropyl ether, diglyme, tert-butyl methyl ether, dimethoxyethane, ethylene glycol diethyl ether, tetrahydrofuran, 1,4-dioxane, etc.); amides (for example, N,N-dimethylformamide, N,N-dimethylacetamide, N-methylpyrrolidone, etc.); sulfoxides (for example, dimethyl sulfoxide etc.); nitriles (for example, acetonitrile, propionitrile, benzonitrile, etc.); ketones (for example, acetone, methyl ethyl ketone, methyl isobutyl ketone, etc.); and ester compounds (for example, methyl acetate, ethyl acetate, etc.). In the case where highly water-miscible alcohols, ethers, amides, sulfoxides, nitriles, ketones or esters are used as the solvent, the water content of the solvent may be up to about 50%. Among the above examples, more preferred is methanol, water-containing methanol, ethanol, water-containing ethanol, methylene chloride, ethyl acetate or acetonitrile.

Production of optically active
2-substituted-1,2,3,4-tetrahydroquinolines

In an embodiment of the present invention, 2-substituted-1,2,3,4-tetrahydroquinolines can be efficiently produced by the reaction route shown below. The reaction formula of the present invention is as shown below. The "hydrogen source" in the following reaction formula means a hydrogen donor.

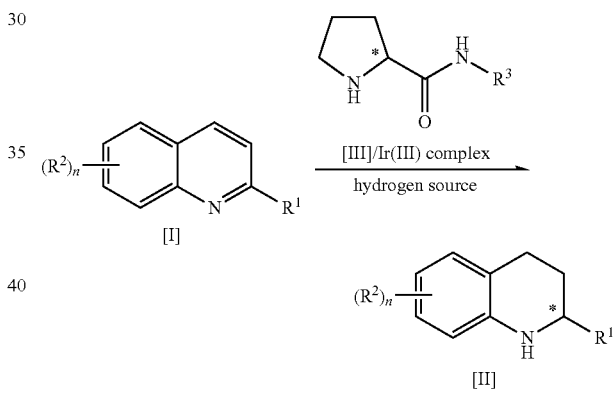

That is, by reducing a quinoline compound represented by general formula [I]:

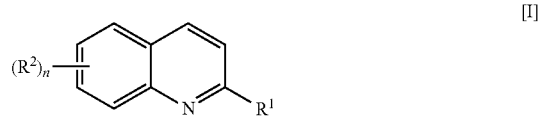

(wherein $R^1$ represents an optionally substituted alkyl group, an optionally substituted aryl group, an optionally substituted aralkyl group, an optionally substituted cycloalkyl group or an optionally substituted heteroaryl group, $R^2$ represents a hydrogen atom, an optionally substituted alkyl group, an optionally substituted aryl group, an optionally substituted aralkyl group, an optionally substituted cycloalkyl group, an optionally substituted heteroaryl group, an optionally substituted hydroxyl group, an optionally substituted thiol group, an optionally substituted amino group, an optionally substituted carbamoyl group, an optionally substituted aryloxy group, an optionally substituted heteroaryloxy group, a carboxyl group, an esterified carboxyl group, a cyano group, a nitro group or a halogen atom, $R^2$ is bound to the quinoline ring at any one of positions 5 to 8, n is an integer of 1 to 4, and when n is not less than 2, $R^2$ groups adjacent to each other may join together to form a ring), in the presence of a hydrogen donor compound and an iridium (III) complex having a chiral prolinamide compound as a ligand, an optically active 2-substituted-1,2,3,4-tetrahydroquinoline represented by formula [II]:

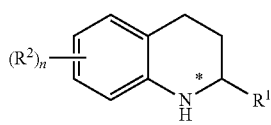

[II]

(wherein $R^1$, $R^2$ and n are as defined in formula [I], and the symbol "*" indicates that the carbon atom is a chiral center) can be produced.

<Starting Material>

In the production of optically active 2-substituted-1,2,3,4-tetrahydroquinolines, a quinoline compound represented by general formula [I]:

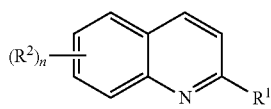

[I]

(each symbol in the formula is as defined in the previously described formula [I])

(hereinafter also referred to as compound [I] in a simple way) is used as a starting material of asymmetric hydrogenation in the present invention.

In compound [I], the "alkyl" moiety in the optionally substituted alkyl group represented by $R^2$ is preferably a straight or branched alkyl group having 1 to 20 carbon atoms. The specific examples include methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl and octadecyl.

The "aryl" moiety in the optionally substituted aryl group represented by $R^1$ is, for example, an aromatic hydrocarbon group having 6 to 14 carbon atoms. The specific examples include phenyl, naphthyl and anthranil.

The "aralkyl" moiety in the optionally substituted aralkyl group represented by $R^1$ is, for example, an alkyl group having 1 to 3 carbon atoms and being substituted by the above-defined "aryl" moiety instead of a hydrogen atom. The specific examples include benzyl, phenylethyl, phenylpropyl and naphthylmethyl.

The "heteroaryl" moiety in the optionally substituted heteroaryl group represented by $R^1$ is, for example, a heteroaryl group having 5 to 14 carbon atoms. The specific examples include furanyl, thienyl, oxazolyl, isoxazolyl, thiazolyl, isothiazolyl, pyrrolyl, imidazolyl, pyrazolyl, pyridyl, pyrimidinyl, pyrazinyl, phthalazinyl, triazinyl, indolyl, isoindolyl, quinolinyl, isoquinolinyl and dibenzofuranyl.

The "cycloalkyl" moiety in the optionally substituted cycloalkyl group represented by $R^1$ is, for example, a cycloalkyl group having 3 to 7 carbon atoms. The specific examples include cyclopropyl, cyclobutyl, cyclopentyl, cyclohexyl and cycloheptyl.

Examples of the substituting group (substituent) in the optionally substituted alkyl group, the optionally substituted aryl group, the optionally substituted aralkyl group, the optionally substituted heteroaryl group and the optionally substituted cycloalkyl group which are all represented by $R^1$ are the same as those of substituting group (A) described above.

Examples of the substituting group in the optionally substituted alkyl group, the optionally substituted aryl group, the optionally substituted aralkyl group, the optionally substituted heteroaryl group and the optionally substituted cycloalkyl group which are all represented by $R^2$ are the same as those of substituting group (A) described above.

Examples of the substituting group in the optionally substituted hydroxyl group, the optionally substituted thiol group, the optionally substituted amino group and the optionally substituted carbamoyl group which are all represented by $R^2$ include straight or branched alkyl groups having 1 to 6 carbon atoms (for example, methyl, ethyl, propyl, isopropyl, butyl, isobutyl, tert-butyl, pentyl, hexyl, etc.), aralkyl groups having 7 to 12 carbon atoms (for example, phenylmethyl, phenylethyl, phenylpropyl, naphthylmethyl, etc.), alkyl halide groups (for example, monofluoromethyl, difluoromethyl, trifluoromethyl, difluoroethyl, trifluoroethyl, trichloromethyl, etc.), carbonyl groups (for example, methylcarbonyl, ethylcarbonyl, phenylcarbonyl, methoxycarbonyl, phenoxycarbonyl, etc.), sulfonyl groups (for example, methylsulfonyl, toluenesulfonyl, trifluoromethylsulfonyl, etc.), and silyl groups (for example, trimethylsilyl, triphenylsilyl, tert-butyldimethylsilyl, etc.).

Examples of the substituting group in the optionally substituted aryloxy group and the optionally substituted heteroaryloxy group which are all represented by $R^2$ are the same as those of substituting group (A) described above.

Examples of the esterified carboxyl group represented by $R^2$ include alkoxycarbonyl groups (for example, methoxycarbonyl etc.) and aryloxycarbonyl groups (for example, phenoxycarbonyl etc.).

Examples of the halogen atom represented by $R^2$ include a fluorine, chlorine, bromine or iodine atom.

$R^2$ is bound to the quinoline ring at any one of positions 5 to 8, and n is an integer of 1 to 4. Preferably, n is 1 or 2.

In the case where plural $R^2$ groups are present and $R^2$ groups adjacent to each other join together to form a ring, the ring is, for example, an aliphatic ring such as methylenedioxy, carbonate, acetonide, oxazole, oxazolinone and methyloxazole; or an aromatic ring such as furan, thiophene, pyrrole, benzene, naphthalene and anthracene, and is optionally substituted by any substituting group. In this case, examples of the substituting group are the same as those of substituting group (A) described above.

<Iridium(III) Complex Having a Chiral Prolinamide Compound as a Ligand>

The iridium(III) complex having a chiral prolinamide compound as a ligand used for the production of optically active 2-substituted-1,2,3,4-tetrahydroquinolines is preferably a compound represented by formula [IV]:

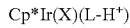

[IV]

(wherein X represents Cl⁻, p-CH₃C₆H₄SO₃⁻, CH₃SO₃⁻, CF₃SO₃⁻, NO₃⁻, BF₄⁻, ClO₄⁻, PF₆⁻, SbF₆⁻, B[3,5-di(trifluoromethyl)phenyl]₄⁻ or B(4-fluorophenyl)₄⁻, L is a compound represented by formula [III]:

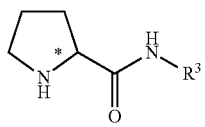

[III]

(wherein $R^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center), and Cp* represents (1,2,3,4,5-η)-pentamethyl-2,4-cyclopentadien-1-yl).

Preferably, the iridium (III) complex has a ligand of formula [III] in which $R^3$ is hydrogen, a 6-quinolinyl group or a 2-methoxy-3-dibenzofuranyl group.

The iridium(III) complex having a chiral prolinamide compound as a ligand is preferably an (R)- or (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) catalyst, or an (R)- or (S)-chloro[(1,2,3,4,5-η)-pentamethyl-2,4-cyclopentadien-1-yl](N-6-quinolinyl-2-pyrrolidinecarboxamidato-κN1, κN2)iridium(III) catalyst.

It is also preferred that the iridium(III) complex having a chiral prolinamide compound as a ligand is an (R)- or (S)-chloro[(1,2,3,4,5-η)-pentamethyl-2,4-cyclopentadien-1-yl](2-pyrrolidinecarboxamidato-κN1, κN2)iridium(III) catalyst.

The iridium(III) complex having a chiral prolinamide compound as a ligand is preferably crystalline.

The chiral prolinamide compound as the ligand of the iridium(III) complex is preferably a compound represented by formula [III]:

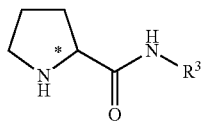

[III]

(wherein $R^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center).

The chiral prolinamide compound is preferably (R)- or (S)-prolinamide or (R)- or (S)-proline heteroaryl amide, and more preferably (R)— or (S)-proline heteroaryl amide. A preferable chiral proline heteroaryl amide compound is (R)— or (S)—N-(6-quinolinyl)-2-pyrrolidinecarboxamide, (R)— or (S)—N-(2-methoxy-3-dibenzofuranyl)-2-pyrrolidinecarboxamide or the like.

The amount of the iridium (III) complex having a chiral prolinamide compound as a ligand used for the reaction is usually about 0.1 to 10 mol %, and preferably about 0.2 to 5 mol % per mole of compound [I].

<Hydrogen Donor Compound>

Examples of the hydrogen donor compound used for the production of optically active 2-substituted-1,2,3,4-tetrahydroquinolines include formic acid, ammonium formate, sodium formate, potassium formate and 2-propanol, and particularly preferred is formic acid. When formic acid is used as the hydrogen donor compound, it is preferable to use a tertiary amine such as triethylamine together therewith. The amount of the hydrogen donor compound used for the reaction is usually about 2 to 40 mol, and preferably about 4 to 20 mol per mole of compound [I].

<Reaction>

In an preferable embodiment, the reducing reaction is conducted as follows: compound [I] is preferably dissolved in a solvent as described in the section "solvent" below, an iridium (III) complex having a chiral prolinamide compound as a ligand is added and dissolved in the solution, and a hydrogen donor compound is added to allow the reaction to proceed.

The reaction temperature of this reaction is usually −70° C. or higher, and preferably about −30 to 40° C.

The reaction time in the present invention is not particularly limited, but is usually 1 minute to 72 hours, preferably 3 minutes to 48 hours, and more preferably 10 minutes to 20 hours.

After the completion of the reaction, the desired optically active tetrahydroquinoline can be obtained by known treatments such as concentration, extraction, filtration and washing. If needed, crystallization, recrystallization, salt formation with an achiral acid such as hydrochloric acid, sulfuric acid, methanesulfonic acid, formic acid and trifluoroacetic acid, followed by recrystallization, and chemical optical resolution using chiral mandelic, tartaric, dibenzoyltartaric, ditoluoyl tartaric, 10-camphor sulfonic or malic acid may be employed to obtain the optically active tetrahydroquinoline in a higher optical purity.

<Solvent>

In the production of optically active 2-substituted-1,2,3,4-tetrahydroquinolines, it is preferable to use a solvent. The solvent is not particularly limited and may be an inorganic or organic solvent. Examples of the solvent include acetonitrile, ethyl acetate, isopropyl acetate, N,N-dimethylformamide, tetrahydrofuran, dimethoxyethane, dichloromethane, alcohols such as methanol, ethanol, 2-propanol and ethylene glycol, and mixed solvents of water and the foregoing. The amount of the solvent used for the reaction is usually about 2 to 200 L, and preferably about 5 to 100 L per kilogram of compound [I].

A mixed solvent of formic acid and triethylamine can be used as the hydrogen donor compound as well as the solvent. In the case where a mixed solvent of formic acid and triethylamine is used as the hydrogen donor compound as well as the solvent, the amount of formic acid used for the reaction is usually about 2 to 40 mol, and preferably about 4 to 20 mol per mole of compound [I]. The amount of triethylamine used for the reaction is usually about 0.1 to 1 mol, and preferably about 0.2 to 0.7 mol per mole of formic acid.

<Optically Active 2-substituted-1,2,3,4-tetrahydroquinolines>

The above-described reaction produces an optically active 2-substituted-1,2,3,4-tetrahydroquinoline represented by general formula [II]:

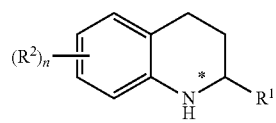

[II]

(wherein $R^1$, $R^2$ and n are as defined in formula [I], and the symbol "*" indicates that the carbon atom is a chiral center).

The optically active 2-substituted-1,2,3,4-tetrahydroquinoline can be used as, for example, a pharmaceutical, an agrochemical, a liquid crystal material, or an intermediate of the foregoing.

EXAMPLES

Hereinafter, the present invention will be illustrated by Examples, but is not limited thereto.
<Measurement Methods>
Melting points were measured with Micro Melting Point System MP (manufactured by Yanagimoto Manufacturing Co., Ltd.).
The elemental analyses of iridium were performed with iCAP6500 Duo ICP atomic emission spectrometer (manufactured by Thermo Fisher Scientific K.K.).
Infrared spectra (IR) were recorded on FT/IR-4100 (manufactured by JASCO Corporation).
Far-infrared spectra were recorded on IFS-66 V/s (manufactured by Bruker Japan Co., Ltd.) and the embedding medium used was polyethylene.
Nuclear magnetic resonance (NMR) spectra were recorded on Gemini-200 (manufactured by Varian Medical Systems, Inc.). The internal standard used was TMS (tetramethylsilane), the solvent used was $CDCl_3$, $CD_3OD$ or $DMSO-d_6$, and the measurement was performed at room temperature. The measured values were expressed in $\delta$ (ppm).
Specific rotations were measured with P-1020 (manufactured by JASCO Corporation).
X-ray powder diffraction patterns were measured with MiniFlexII (manufactured by Rigaku Corporation).
Optical purities were determined with a high-performance liquid chromatograph (HPLC) (LC10A; manufactured by Shimadzu Corporation) equipped with a chiral column, by calculating the peak area ratio of a pair of enantiomers.
The solvents and reagents used in the reactions described below are commercial products if not otherwise specified.
In the following examples, a (1,2,3,4,5-η)-pentamethyl-2,4-cyclopentadien-1-yl moiety is abbreviated to Cp*, 2-pyrrolidinecarboxamide is abbreviated to PA, N-6-quinolinyl-2-pyrrolidinecarboxamide is abbreviated to PQA, and N-(2-methoxy-3-dibenzofuranyl)-2-pyrrolidinecarboxamide is abbreviated to PMDBFA; or in some cases, the full names and their abbreviations are shown together.

Example 1

Synthesis of crystalline (R)-chloro[(1,2,3,4,5-η)-pentamethyl-2,4-cyclopentadien-1-yl](2-pyrrolidinecarboxamidato-κN1, κN2)iridium(III) (Cp*Ir (Cl⁻)(R-PA-H⁺))

To 40 ml of methylene chloride, 1.593 g of a pentamethylcyclopentadienyl iridium(III) chloride dimer ([Cp*IrCl$_2$]$_2$), 502 mg of (R)-prolinamide and 425 mg of triethylamine were successively added, and the mixture was continuously stirred at room temperature overnight. To the reaction mixture, 10 ml of a 20% aqueous sodium chloride solution was added, and the mixture was stirred for about 30 minutes and then left to stand. The resulting layers were separated.
The aqueous layer was extracted with 10 ml of methylene chloride, and then the organic layers were combined and washed with 10 ml of a 20% aqueous sodium chloride solution. Further, this aqueous layer was extracted with 10 ml of methylene chloride, and then the organic layers were combined and dried over 10 g of anhydrous sodium sulfate overnight. The desiccant was filtered off and washed with methylene chloride, and then the filtrate was concentrated in vacuo. To the concentrated residue, 20 ml of tetrahydrofuran/diisopropyl ether (1/1) was added, and the mixture was stirred at 35 to 40° C. for about 1 hour. The precipitate was collected by suction filtration, washed with 10 ml of tetrahydrofuran/diisopropyl ether (1/1), and then dried in vacuo at 40 to 50° C. for 5 hours to give 1.813 g of (R)-chloro[(1,2,3,4,5-η)-pentamethyl-2,4-cyclopentadien-1-yl](2-pyrrolidinecarboxamidato-κN1, κN2)iridium(III) (Cp*Ir(Cl⁻)(R-PA-H⁺)) as a yellow crystalline powder.
Melting point: 174.8° C.
Elemental analysis: $C_{15}H_{24}ClIrN_2O$ (476.01) calculated value (%) C, 37.84; H, 5.08; N, 5.88; Ir, 40.4 found value (%) C, 37.81; H, 5.07; N, 5.93; Ir40.7
IR (KBr): 3429, 3282, 1599 cm$^{-1}$
$^1$H-NMR (200 MHz, CDCl$_3$): δ 1.60-2.28 (4H, m, 2×CH$_2$), 1.70 (15H, s, 5Me of Cp*), 2.71-2.93 (1H, m, one of NCH$_2$), 3.41-3.55 (1H, m, one of NCH$_2$), 3.89-4.01 (1H, m, NCH), 4.96 (2H, br, 2×NH).
$^{13}$C-NMR (50.3 MHz, CDCl$_3$): δ 9.1 (5Me of Cp*), 27.1 (CH$_2$), 28.2 (CH$_2$), 54.3 (NCH$_2$), 62.9 (NCH), 84.4 (ArC of Cp*), 183.5 (C=O).

Example 2

Synthesis of crystalline (R)-chloro[(1,2,3,4,5-η)-pentamethyl-2,4-cyclopentadien-1-yl](2-pyrrolidinecarboxamidato-κN1, κN2)iridium(III) (Cp*Ir (Cl⁻)(R-PA-H⁺))

To a suspension of 3.59 g of a pentamethylcyclopentadienyl iridium(III) chloride dimer ([Cp*IrCl$_2$]$_2$) and 1.08 g of (R)-prolinamide in 90 ml of acetonitrile, 1.38 ml of triethylamine was added dropwise with stirring under argon stream at room temperature, and the mixture was further stirred at room temperature for about 1.5 hours. After removal of acetonitrile by evaporation in vacuo, 60 ml of a saturated aqueous sodium chloride solution and 30 ml of water were added to the residue, and the mixture was extracted with chloroform 3 times (the volumes of chloroform were 45 ml, 30 ml and 30 ml). The extracts were collected, washed with 45 ml of a saturated aqueous sodium chloride solution once, and dried over anhydrous sodium sulfate. The desiccant was removed, and the filtrate was concentrated in vacuo. To the residual concentrate, 15 ml of acetonitrile was added, and the solution was cooled to below freezing for crystallization.
The crystalline precipitate was collected by filtration, washed with acetonitrile/diisopropyl ether (1/3), and then dried in vacuo at 60° C. for 3 hours to give 3.289 g of (R)-chloro[(1,2,3,4,5-η)-pentamethyl-2,4-cyclopentadien-1-yl](2-pyrrolidinecarboxamidato-κN1, κN2)iridium(III) (Cp*Ir(Cl⁻)(R-PA-H⁺)) as a yellow crystalline powder.
Melting point: 210° C. (with decomposition)
Elemental analysis: $C_{15}H_{24}ClIrN_2O$ (476.01) calculated value (%) C, 37.84; H, 5.08; N, 5.88; Ir, 40.4 found value (%) C, 37.82; H, 5.08; N, 5.94; Ir, 40.7
Water content (Karl Fischer method): 0.17%

Example 3

Synthesis of crystalline (S)-chloro[(1,2,3,4,5-η)-pentamethyl-2,4-cyclopentadien-1-yl](2-pyrrolidinecarboxamidato-κN1, κN2)iridium(III) (Cp*Ir(Cl⁻)(S-PA-H⁺))

To 40 ml of methylene chloride, 1.593 g of a pentamethylcyclopentadienyl iridium(III) chloride dimer ([Cp*

IrCl₂]₂), 502 mg of (S)-prolinamide and 425 mg of triethylamine were successively added, and the mixture was continuously stirred at room temperature overnight. To the reaction mixture, 10 ml of a 20% aqueous sodium chloride solution was added, and the mixture was stirred for about 30 minutes and then left to stand. The resulting layers were separated. The aqueous layer was extracted with 10 ml of methylene chloride, and then the organic layers were combined and washed with 10 ml of a 20% aqueous sodium chloride solution. Further, this aqueous layer was extracted with 10 ml of methylene chloride, and then the organic layers were combined and dried over 10 g of anhydrous sodium sulfate overnight. The desiccant was filtered off and washed with methylene chloride, and then the filtrate was concentrated in vacuo. To the concentrated residue, 20 ml of tetrahydrofuran/diisopropyl ether (1/1) was added, and the mixture was stirred at 35 to 40° C. for about 1 hour. The precipitate was collected by suction filtration, washed with 10 ml of tetrahydrofuran/diisopropyl ether (1/1), and then dried in vacuo at 40 to 50° C. for 5 hours to give 1.796 g of (S)-chloro[(1,2,3,4,5-η)-pentamethyl-2,4-cyclopentadien-1-yl](2-pyrrolidinecarboxamidato-κN1, κN2)iridium(III) (Cp*Ir(Cl⁻)(S-PA-H⁺)) as a yellow crystalline powder.

Melting point: 173.5° C.

IR (KBr): 3433, 3281, 1599 cm⁻¹

$^1$H-NMR (200 MHz, CDCl₃): δ 1.60-2.28 (4H, m, 2×CH₂), 1.70 (15H, s, 5Me of Cp*), 2.71-2.93 (1H, m, one of NCH₂), 3.41-3.56 (1H, m, one of NCH₂), 3.88-4.00 (1H, m, NCH), 4.96 (2H, br, 2×NH).

$^{13}$C-NMR (50.3 MHz, CDCl₃): δ 9.1 (5Me of Cp*), 27.1 (CH₂), 28.2 (CH₂), 54.3 (NCH₂), 62.9 (NCH), 84.5 (ArC of Cp*), 183.6 (C=O).

Example 4

Synthesis of crystalline (S)-chloro[(1,2,3,4,5-η)-pentamethyl-2,4-cyclopentadien-1-yl](2-pyrrolidinecarboxamidato-κN1, κN2)iridium(III) (Cp*Ir(Cl⁻)(S-PA-H⁺))

To a suspension of 3.19 g of a pentamethylcyclopentadienyl iridium(III) chloride dimer ([Cp*IrCl₂]₂) and 0.959 g of (S)-prolinamide in 80 ml of acetonitrile, 1.23 ml of triethylamine was added dropwise with stirring under argon stream at room temperature, and the mixture was further stirred at room temperature for about 1 hour. After removal of acetonitrile by evaporation in vacuo, 50 ml of a saturated aqueous sodium chloride solution and 25 ml of water were added to the residue, and the mixture was extracted with chloroform 3 times (the volumes of chloroform were 40 ml, 30 ml and 30 ml). The extracts were collected, washed with 40 ml of a saturated aqueous sodium chloride solution once, and dried over anhydrous sodium sulfate. The desiccant was removed, and the filtrate was concentrated in vacuo. To the concentrated residue, 12 ml of acetonitrile was added and the mixture was heated to 50° C. for dissolution. To the solution, 24 ml of diisopropyl ether was added, and the solution was cooled to below freezing for crystallization.

The crystalline precipitate was collected by filtration, washed with acetonitrile/diisopropyl ether (1/3), and then dried in vacuo at 60° C. for 3 hours to give 3.028 g of (S)-chloro[(1,2,3,4,5-η)-pentamethyl-2,4-cyclopentadien-1-yl](2-pyrrolidinecarboxamidato-κN1, κN2)iridium(III) (Cp*Ir(Cl⁻)(S-PA-H⁺)) as a yellow crystalline powder.

Figure 2:
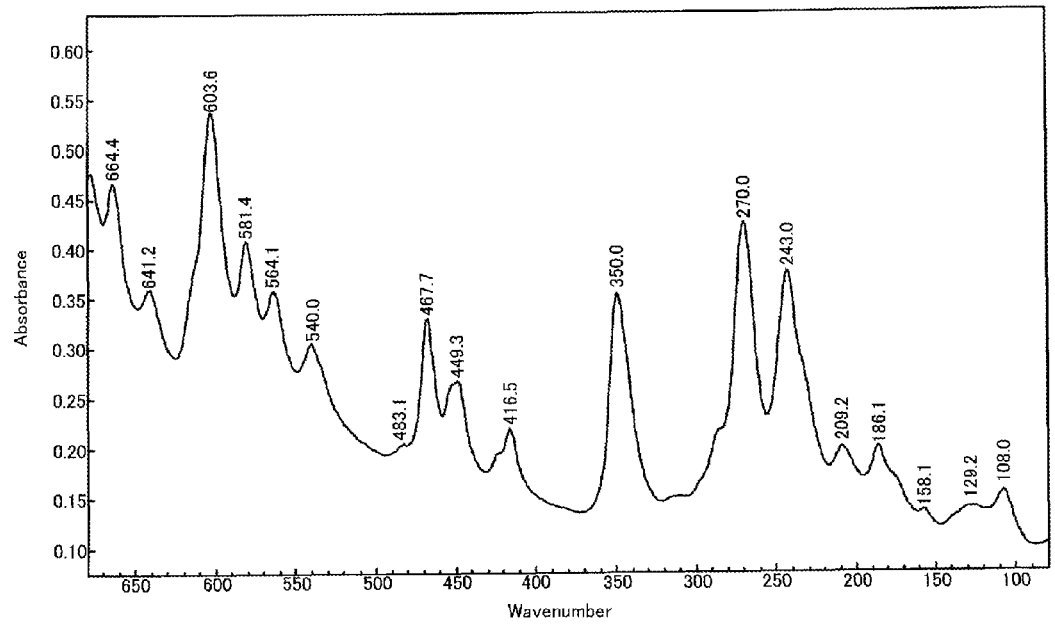
FIG. 2 shows a far-infrared spectrum of the crystalline (S)-chloro[(1,2,3,4,5-η)-pentamethyl-2,4-cyclopentadien-1-yl](2-pyrrolidinecarboxamidato-κN1, κN2)iridium(III) produced in Example 4.
Figure 3:
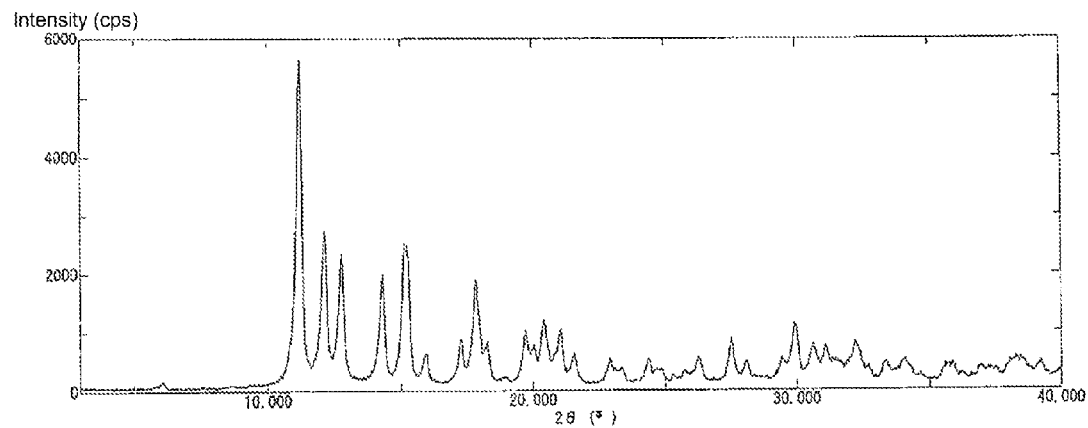
FIG. 3 shows an X-ray powder diffraction pattern of the crystalline (S)-chloro[(1,2,3,4,5-η)-pentamethyl-2,4-cyclopentadien-1-yl](2-pyrrolidinecarboxamidato-κN1, κN2)iridium(III) produced in Example 4.

The IR (KBr) chart, far-infrared spectrum and X-ray powder diffraction pattern of this product are shown in FIGS. 1, 2 and 3, respectively.

Melting point: 210° C. (with decomposition)

Water content (Karl Fischer method): 0.30%

Elemental analysis: C₁₅H₂₄ClIrN₂O (476.01) calculated value (%) C, 37.84; H, 5.08; N, 5.88 found value (%) C, 37.74; H, 5.08; N, 5.89

IR (KBr): 3433, 1609, 1449, 917 cm⁻¹

Far-infrared spectrum: 664, 641, 604, 581, 564, 540, 468, 449, 417, 350, 270 cm⁻¹

$^1$H-NMR (200 MHz, CDCl₃): δ 1.60-2.28 (4H, m, 2×CH₂), 1.70 (15H, s, 5Me of Cp*), 2.71-2.93 (1H, m, one of NCH₂), 3.40-3.60 ($^1$H, m, one of NCH₂), 3.85-4.05 (1H, m, NCH), 4.75-5.00 (1H, br, NH), 4.90 (1H, s, NH).

$^1$H-NMR (200 MHz, DMSO-d₆): δ 1.46-1.93 (4H, m), 1.63 (15H, s, 5Me of Cp*), 2.48-2.74 (1H, m, one of NCH₂), 3.23-3.38 (1H, m, one of NCH₂), 3.45-3.58 (1H, m, NCH), 5.04 (1H, br s, CONH), 6.15-6.30 (6.23 centered, 1H, br, NH).

$^{13}$C-NMR (50.3 MHz, DMSO-d₆): 8.6 (5Me of Cp*), 26.1 (CH₂), 27.8 (CH₂), 53.6 (NCH₂), 62.1 (NCH), 83.7 (ArC of Cp*), 182.2 (C=O).

Reference Example 1

Figure 4:
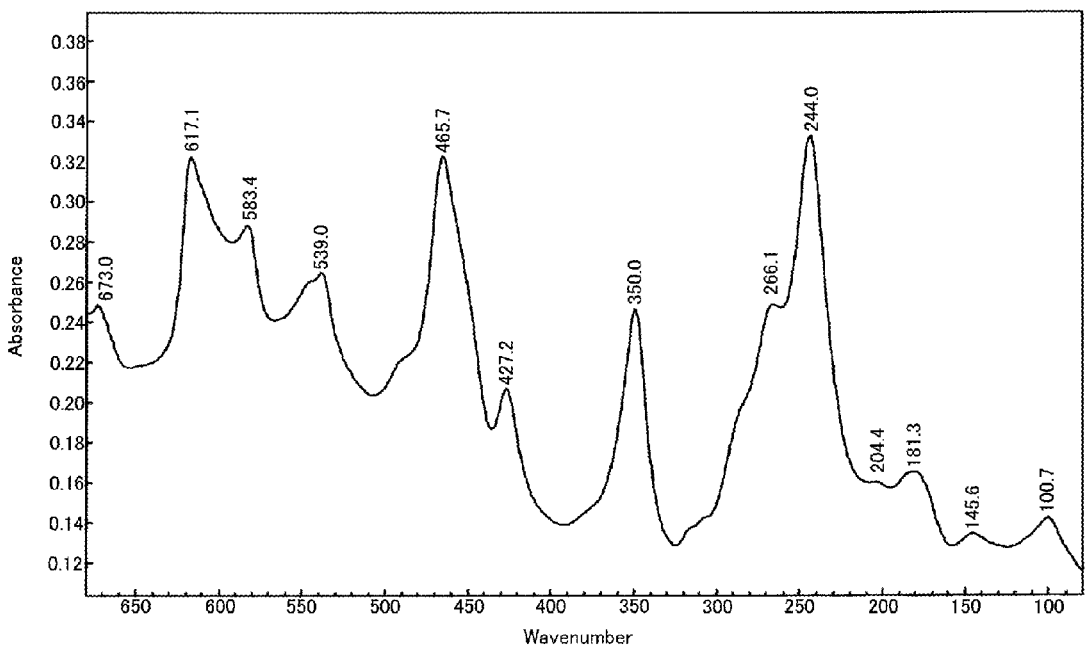
FIG. 4 shows a far-infrared spectrum of the powder produced in Reference Example 1.

According to the method of Winfried Hoffmueller et al. (Winfried Hoffmueller, Kurt Polborn, Joerg Knizek, Heinrich Noeth and Wolfgang Beck, Z. Anorg. Allg. Chem. 1997, 623, 1903-1911), compound 10 described in this reference was prepared as a powder. The far-infrared spectrum of this product is shown in FIG. 4.

Far-infrared spectrum: 617, 583, 539, 466, 427, 350, 266, 244 cm⁻¹

Example 5

Synthesis of crystalline (R)-chloro[(1,2,3,4,5-η)-pentamethyl-2,4-cyclopentadien-1-yl](N-6-quinolinyl-2-pyrrolidinecarboxamidato-κN1, κN2)iridium(III) (Cp*Ir(Cl⁻)(R-PQA-H⁺))

To 50 ml of acetonitrile, 1.593 g of a pentamethylcyclopentadienyl iridium(III) chloride dimer ([Cp*IrCl₂]₂), 502 mg of (R)—N-6-quinolinyl-2-pyrrolidinecarboxamide and 425 mg of triethylamine were successively added, and the mixture was continuously stirred at room temperature overnight. The precipitate was collected by suction filtration, washed successively with 15 ml of acetonitrile/water (20/1) and 10 ml of acetonitrile, and then dried in vacuo at 40 to 50° C. for 5 hours to give 2.175 g of (R)-chloro[(1,2,3,4,5-η)-pentamethyl-2,4-cyclopentadien-1-yl](N-6-quinolinyl-2-pyrrolidinecarboxamidato-κN1, κN2)iridium(III) (Cp*Ir(Cl⁻)(R-PQA-H⁺)) as a yellow crystalline powder.

Melting point: 243.8° C.

IR (KBr): 3446, 3128, 1576 cm⁻¹

$^1$H-NMR (200 MHz, CD₃OD): δ 1.37 (15H, s, 5Me of Cp*), 1.66-2.32 (4H, m, 2×CH₂), 3.18-3.36 (1H, m, one of NCH₂), 3.48-3.59 (1H, m, one of NCH₂), 4.06-4.14 (1H, m, NCH), 7.50 (1H, dd, J=8.2, 4.2 Hz), 7.76 (1H, dd, J=8.6, 2.2 Hz), 7.79 (1H, br s), 7.96 (1H, br d, J=8.6 Hz), 8.29 (1H, br dd, J=8.2, 1.6 Hz), 8.75 (1H, dd, J=4.2, 1.6 Hz).

$^{13}$C-NMR (50.3 MHz, CD₃OD): δ 8.9 (5Me of Cp*), 27.9 (CH₂), 31.1 (CH₂), 56.0 (NCH₂), 66.3 (NCH), 87.1 (ArC of Cp*), 122.7 (CH), 125.7 (CH), 128.8 (CH), 130.2 (quaternary), 133.2 (CH), 138.0 (CH), 146.9 (quaternary), 149.2 (quaternary), 150.3 (CH), 183.2 (C=O).

Example 6

Synthesis of crystalline (S)-chloro[(1,2,3,4,5-η)-pentamethyl-2,4-cyclopentadien-1-yl](N-6-quinolinyl-2-pyrrolidinecarboxamidato-κN1, κN2)iridium (III) (Cp*Ir(Cl⁻)(S-PQA-H⁺))

To 50 ml of acetonitrile, 1.593 g of a pentamethylcyclopentadienyl iridium(III) chloride dimer ([Cp*IrCl$_2$]$_2$), 502 mg of (S)—N-6-quinolinyl-2-pyrrolidinecarboxamide and 425 mg of triethylamine were successively added, and the mixture was continuously stirred at room temperature overnight. The precipitate was collected by suction filtration, washed successively with 15 ml of acetonitrile/water (20/1) and 10 ml of acetonitrile, and then dried in vacuo at 40 to 50° C. for 5 hours to give 2.322 g of (S)-chloro[(1,2,3,4,5-η)-pentamethyl-2,4-cyclopentadien-1-yl](N-6-quinolinyl-2-pyrrolidinecarboxamidato-κN1, κN2)iridium(III) (Cp*Ir(Cl⁻)(S-PQA-H⁺)) as a yellow crystalline powder.

Melting point: 241.8° C.

IR (KBr): 3433, 3130, 1576 cm⁻¹

$^1$H-NMR (200 MHz, CD$_3$OD): δ 1.37 (15H, s, 5Me of Cp*), 1.66-2.32 (4H, m, 2×CH$_2$), 3.16-3.36 (1H, m, one of NCH$_2$), 3.48-3.59 (1H, m, one of NCH$_2$), 4.06-4.14 (1H, m, NCH), 7.50 (1H, dd, J=8.2, 4.4 Hz), 7.76 (1H, dd, J=8.6, 2.2 Hz), 7.79 (1H, br s), 7.96 (1H, br d, J=8.6 Hz), 8.29 (1H, br dd, J=8.2, 1.6 Hz), 8.75 (1H, dd, J=4.4, 1.6 Hz).

$^{13}$C-NMR (50.3 MHz, CD$_3$OD): δ 8.9 (5Me of Cp*), 27.9 (CH$_2$), 31.1 (CH$_2$), 56.0 (NCH$_2$), 66.3 (NCH), 87.1 (ArC of Cp*), 122.7 (CH), 125.7 (CH), 128.8 (CH), 130.2 (quaternary), 133.2 (CH), 138.0 (CH), 146.9 (quaternary), 149.2 (quaternary), 150.3 (CH), 183.2 (C=O).

Example 7

Synthesis of crystalline (R)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) (Cp*Ir(Cl⁻)(R-PMDBFA-H⁺))

To 50 ml of acetonitrile, 1.593 g of a pentamethylcyclopentadienyl iridium(III) chloride dimer ([CP*IrCl$_2$]$_2$), 1.361 g of (R)—N-(2-methoxy-3-dibenzofuranyl)-2-pyrrolidinecarboxamide and 425 mg of triethylamine were successively added, and the mixture was continuously stirred at room temperature overnight. After addition of 7.0 ml of water, the reaction mixture was stirred for about 30 minutes. Then, the precipitate was collected by suction filtration, washed successively with 20 ml of acetonitrile/water (9/1) and 10 ml of acetonitrile, and then dried in vacuo at 40 to 50° C. for 5 hours to give 2.623 g of (R)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) (Cp*Ir(Cl⁻)(R-PMDBFA-H⁺)) as a yellow crystalline powder.

Melting point: not lower than 300° C.

IR (KBr): 3446, 3214, 1581 cm⁻¹

$^1$H-NMR (200 MHz, CD$_3$OD): δ 1.38 (15H, s, 5Me of Cp*), 3.93 (3H, s, OMe), 7.48 (1H, s, ArH), 7.57 (1H, s, ArH).

Example 8

Synthesis of crystalline (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) (Cp*Ir(Cl⁻)(S-PMDBFA-H⁺))

To 50 ml of acetonitrile, 1.593 g of a pentamethylcyclopentadienyl iridium(III) chloride dimer ([Cp*IrCl$_2$]$_2$), 1.361 g of (S)—N-(2-methoxy-3-dibenzofuranyl)-2-pyrrolidinecarboxamide and 425 mg of triethylamine were successively added, and the mixture was continuously stirred at room temperature overnight. After addition of 7.0 ml of water, the reaction mixture was stirred for about 30 minutes. Then, the precipitate was collected by suction filtration, washed successively with 20 ml of acetonitrile/water (9/1) and 10 ml of acetonitrile, and then dried in vacuo at 40 to 50° C. for 5 hours to give 2.655 g of (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) (Cp*Ir(Cl⁻)(S-PMDBFA-H⁺)) as a yellow crystalline powder.

Melting point: not lower than 300° C.

IR (KBr): 3433, 3215, 1580 cm⁻¹

$^1$H-NMR (200 MHz, CD$_3$OD): δ 1.38 (15H, s, 5Me of Cp*), 3.93 (3H, s, OMe), 7.48 (1H, s, ArH), 7.58 (1H, s, ArH).

Example 9

Asymmetric Reduction of 2-methylquinoline

In 60 ml of methylene chloride, 1.00 g of 2-methylquinoline was dissolved, and 66.5 mg (2.0 mol %) of crystalline (S)-chloro[(1,2,3,4,5-η)-pentamethyl-2,4-cyclopentadien-1-yl](2-pyrrolidinecarboxamidato-κN1, κN2)iridium(III) (Cp*Ir(Cl⁻)(S-PA-H⁺)) was added. After cooling to −20° C., 8.4 ml of a mixed solvent of formic acid/triethylamine (molar ratio: 5/2) was added dropwise, and the mixture was continuously stirred at the same temperature for 20 hours. Then, the reaction was completed. The reaction mixture was basified with an aqueous potassium carbonate solution and then the resulting layers were separated. The organic layer was washed with water and concentrated to give 1.05 g of 2-methyl-1,2,3,4-tetrahydroquinoline as an oil.

This product was analyzed for optical purity with the use of an optically active column (CHIRALCEL OJ-RH; manufactured by Daicel Chemical Industries, Ltd.). As a result, the S-enantiomer was in excess and the optical purity was 90.4% ee.

Specific rotation: $[\alpha]_D^{20}$ −78.3° (c=1.0, MeOH)

$^1$H-NMR (200 MHz, CDCl$_3$): δ 1.21 (3H, d, J=6.2 Hz, 2-Me), 1.58 (1H, dddd, J=12.8, 11.0, 9.9, 5.9 Hz, one of 3-H$_2$), 1.93 (1H, dddd, J=12.8, 5.5, 3.7, 2.9 Hz, one of 3-H$_2$), 2.64-2.94 (2H, m, 4-H$_2$), 3.30-3.85 (1H, br, 1-H), 3.39 (1H, dqd, J=9.9, 6.2, 2.9 Hz, 2-H), 6.44-6.49 (1H, m, ArH), 6.60 (1H, td, J=7.3, 1.2 Hz, ArH), 6.91-7.01 (2H, m, ArH).

$^{13}$C-NMR (50.3 MHz, CDCl$_3$): δ 22.6 (2-Me), 26.6 (3-C), 30.1 (4-C), 47.2 (2-C), 114.0 (ArC), 117.0 (ArC), 121.1 (quaternary ArC), 126.7 (ArC), 129.3 (ArC), 144.7 (quaternary ArC).

Example 10

Asymmetric Reduction of 6-fluoro-2-methylquinoline

The same procedures as in Example 7 were performed except that 6-fluoro-2-methylquinoline was used as a starting material, and 6-fluoro-2-methyl-1,2,3,4-tetrahydroquinoline was obtained. The S-enantiomer was in excess and the optical purity was 95.4% ee.

Example 11

Asymmetric Reduction of 6-methoxy-2-methylquinoline

The same procedures as in Example 7 were performed except that 6-methoxy-2-methylquinoline was used as a starting material, and 6-methoxy-2-methyl-1,2,3,4-tetrahydroquinoline was obtained. The S-enantiomer was in excess and the optical purity was 80.4% ee.

Example 12

Asymmetric Reduction of 2-methylquinoline

To 10 ml of methylene chloride, 55.6 mg of a pentamethylcyclopentadienyl iridium(III) chloride dimer ([Cp*IrCl$_2$]$_2$) (1.0 mol % as a dimer), 16.7 mg of (S)-prolinamide and 15.6 mg of triethylamine were added, and the mixture was stirred under argon atmosphere at room temperature for about 30 minutes to give a catalyst-containing mixture.

In 60 ml of methylene chloride, 1.00 g of 2-methylquinoline was dissolved, and the catalyst-containing mixture was added. After cooling to −10° C., 8.4 ml of a mixed solvent of formic acid/triethylamine (molar ratio: 5/2) was added dropwise, and the mixture was stirred at the same temperature overnight to give 2-methyl-1,2,3,4-tetrahydroquinoline. The S-enantiomer was in excess and the optical purity was 86.4% ee.

Comparative Example 1

Asymmetric Reaction of 2-Methylquinoline Using a Crystalline Iridium Catalyst (Catalytic Amount: 0.2 Mol %)

In 60 ml of methylene chloride, 1.00 g of 2-methylquinoline was dissolved, and as a catalyst, 6.7 mg (0.2 mol %) of a crystalline (R)-chloro[(1,2,3,4,5-η)-pentamethyl-2,4-cyclopentadien-1-yl](2-pyrrolidinecarboxamidato-κN1, κN2)iridium(III) complex (Cp*Ir(Cl$^-$)(R-PA-H$^+$)) was added. After cooling to −10° C., 8.4 ml of a mixed solvent of formic acid/triethylamine (molar ratio: 5/2) was added dropwise, and the mixture was stirred at the same temperature for 2 days to give 2-methyl-1,2,3,4-tetrahydroquinoline (degree of conversion: 73%). The R-enantiomer was in excess and the optical purity was 90.2% ee.

Comparative Example 2

Asymmetric Reaction of 2-Methylquinoline Using an Iridium Catalyst-Containing Mixture (Catalytic Amount: 0.2 Mol %)

To 10 ml of methylene chloride, 55.6 mg of a pentamethylcyclopentadienyl iridium(III) chloride dimer ([Cp*IrCl$_2$]$_2$), 16.7 mg of (R)-prolinamide and 15.6 mg of triethylamine were added, and the mixture was stirred under argon atmosphere at room temperature for about 30 minutes to give a catalyst-containing mixture. In 60 ml of methylene chloride, 1.00 g of 2-methylquinoline was dissolved, and a 1/10 amount of the catalyst-containing mixture (equivalent to 0.1 mol % as an iridium chloride dimer) was added. After cooling to −10° C., 8.4 ml of a mixed solvent of formic acid/triethylamine (molar ratio: 5/2) was added dropwise, and the mixture was stirred at the same temperature for 2 days to give 2-methyl-1,2,3,4-tetrahydroquinoline (degree of conversion: 67.4%). The R-enantiomer was in excess and the optical purity was 85.4% ee.

Comparative Example 3

Asymmetric Reaction of 2-Methylquinoline Using an Iridium Catalyst-Containing Mixture Left Unused for One Week after Preparation (Catalytic Amount: 0.2 Mol %)

The same procedures as in Comparative Example 11 were performed except that the catalyst-containing mixture prepared in Example 11 was left at room temperature for one week after the preparation and used as a catalyst, and 2-methyl-1,2,3,4-tetrahydroquinoline was obtained (degree of conversion: 56.9%). The R-enantiomer was in excess and the optical purity was 49.8% ee.

Example 13

Asymmetric Reduction of 2-Phenylquinoline

In 30 ml of 10% hydrous methanol, 1.03 g of 2-phenylquinoline was dissolved, and 47.7 mg (2.0 mol %) of crystalline (S)-chloro[(1,2,3,4,5-η)-pentamethyl-2,4-cyclopentadien-1-yl](2-pyrrolidinecarboxamidato-κN1, κN2)iridium(III) (Cp*Ir(Cl$^-$)(S-PA-H$^+$)) was added. After cooling to −20° C., 6.0 ml of a mixed solvent of formic acid/triethylamine (molar ratio: 5/2) was added dropwise, and the mixture was continuously stirred at the same temperature for 20 hours. Then, the reaction was completed.

The product was identified as 2-phenyl-1,2,3,4-tetrahydroquinoline by NMR. This product was analyzed for optical purity with the use of an optically active column (CHIRALCEL OJ-RH; manufactured by Daicel Chemical Industries, Ltd.). As a result, the R-enantiomer was in excess and the optical purity was 74.1% ee.

After the reaction, the precipitate was collected by filtration, washed with 50% hydrous methanol, and air-dried to give 406 mg of a colorless crystal. This product was (R)-2-phenyl-1,2,3,4-tetrahydroquinoline and the optical purity was 98.3% ee.

Melting point: 56.9° C.

Specific rotation: $[\alpha]_D^{20}$ −69.8° (c=1.0, MeOH)

$^1$H-NMR (200 MHz, CDCl$_3$): δ 1.89-2.19 (2H, m, 3-H$_2$), 2.74 (1H, H$_B$ of ABXX' system, J$_{AB}$=16.3 Hz, J$_{BX}$=J$_{BX'}$=4.8 Hz, one of 4-H$_2$), 2.92 (1H, H$_A$ of ABXX' system, J$_{AB}$=16.3 Hz, J$_{AX}$=10.5 Hz, J$_{AX'}$=5.9 Hz, one of 4-H$_2$), 4.04 (1H, br s, 1-H), 4.44 (1H, dd, J=9.1, 3.7 Hz, 2-H), 6.51-6.57 (1H, m, ArH), 6.65 (1H, td, J=7.3, 1.1 Hz, ArH), 6.96-7.06 (2H, m, ArH), 7.23-7.43 (5H, m, Ph).

$^{13}$C-NMR (50.3 MHz, CDCl$_3$): δ 26.4 (3-C), 31.0 (4-C), 56.2 (2-C), 114.0 (ArC), 117.2 (ArC), 120.9 (quaternary ArC), 126.5 (ArC), 126.9 (ArC), 127.4 (ArC), 128.6 (ArC), 129.3 (ArC), 144.7 (quaternary ArC), 144.8 (quaternary ArC).

Example 14

Asymmetric Reduction of 2-(3-hydroxyphenyl)-5-(3-trifluoromethoxyphenyl)quinoline In 30 ml of methanol, 381 mg of 2-(3-hydroxyphenyl)-5-(3-trifluoromethoxyphenyl)quinoline was dissolved, and 23.8 mg of crystalline (R)-chloro[(1,2,3,4,5-η)-pentamethyl-2,4-cyclopentadien-1-yl](2-pyrrolidinecarboxamidato-κN1, κN2)iridium(III) (Cp*Ir(Cl$^-$)(R-PA-H$^+$)) was added. After cooling to −20° C., 5.0 ml of a mixed solvent of formic acid/triethylamine (molar ratio: 5/2) was added dropwise, and the mixture was continuously stirred at the same temperature for 2 days. Further, the catalyst and the mixed solvent of formic acid/triethylamine were added again in the same amounts as above, and the mixture was continuously stirred for one day. Then, the reaction was completed. The reaction mixture was concentrated in vacuo and extracted with methylene chloride. After basification with an aqueous sodium carbonate solution, the resulting layers were separated. The organic layer was washed with water and concentrated.

The resulting oil was purified by column chromatography, and the fractions eluted by methylene chloride/n-hexane (3/1) were collected and concentrated in vacuo to give 280 mg of an oil.

This product was identified as 1,2,3,4-tetrahydro-2-(3-hydroxyphenyl)-5-(3-trifluoromethoxyphenyl)quinoline by NMR. This product was analyzed for optical purity with the use of an optically active column (CHIRALCEL OJ-RH; manufactured by Daicel Chemical Industries, Ltd.). As a result, the R-enantiomer was in excess and the optical purity was 71.3% ee.

Specific rotation: $[\alpha]_D^{20}$ −17.3 (c=1.04, CHCl$_3$)

$^1$H-NMR (200 MHz, CDCl$_3$): δ 1.74-1.94 (1H, m, one of 3-H$_2$), 2.01-2.11 (1H, m, one of 3-H$_2$), 2.44-2.59 (1H, m, one of 4-H$_2$), 2.73 (1H, H$_A$ of ABXX' system, $J_{AB}$=16.7 Hz, $J_{AX}$=10.0 Hz, $J_{AX'}$=5.1 Hz, one of 4-H$_2$), 4.41 (1H, dd, J=8.8, 3.5 Hz, 2-H), 6.53-6.57 (1H, m, ArH), 6.58-6.61 (1H, m, ArH), 6.74 (1H, ddd, J=8.1, 2.6, 0.9 Hz, ArH), 6.84-6.87 (1H, m, ArH), 6.93 (1H, br d, J=7.8 Hz, ArH), 7.07 (1H, t, J=7.8 Hz, ArH), 7.12-7.27 (5H, m, ArH), 7.33-7.44 (1H, m, ArH).

$^{13}$C-NMR (50.3 MHz, CDCl$_3$): δ 24.7 (3-C), 30.7 (4-C), 55.7 (2-C), 113.3 (ArCH), 113.7 (ArCH), 114.4 (ArCH), 118.2 (quaternary ArC), 118.7 (ArCH), 118.9 (ArCH), 119.1 (ArCH), 121.7 (ArCH), 123.1 (CF$_3$), 126.8 (ArCH), 127.6 (ArCH), 129.3 (ArCH), 129.9 (ArCH), 140.9 (quaternary ArC), 143.8 (quaternary ArC), 144.7 (quaternary ArC), 146.7 (quaternary ArC), 148.9 (quaternary ArC), 155.8 (quaternary ArC).

Reference Example 2

In 8.0 ml of dimethyl sulfoxide, 224 mg of the product purified by column chromatography in Example 12 was dissolved, 283 mg of cesium carbonate and 139 mg of 1,1,2,2-tetrafluoro-1-iodoethane were added, and the mixture was continuously stirred under water-cooling overnight. After the reaction mixture was extracted with methylene chloride, the extract was washed with an aqueous sodium bicarbonate solution, further washed with water 5 times, and then concentrated in vacuo to give 240 mg of an oil.

The resulting oil was purified by column chromatography, and the fractions eluted by methylene chloride/n-hexane (1/10) were collected and concentrated in vacuo to give 221 mg of an oil. This product was identified as 1,2,3,4-tetrahydro-2-[3-(1,1,2,2-tetrafluoroethoxy)phenyl]-5-(3-trifluoromethoxyphenyl)quinoline by NMR. This product was analyzed for optical purity with the use of an optically active column (CHIRALCEL OJ-RH; manufactured by Daicel Chemical Industries, Ltd.). As a result, the R-enantiomer was in excess and the optical purity was 66.8% ee.

Specific rotation: $[\alpha]_D^{20}$ −8.6° (c=0.88, CHCl$_3$)

$^1$H-NMR (200 MHz, CDCl$_3$): δ 1.77-1.96 (1H, m, one of 3-H$_2$), 1.99-2.14 (1H, m, one of 3-H$_2$), 2.53 (1H, H$_B$ of ABXX' system, $J_{AB}$=16.7 Hz, $J_{BX}$=$J_{BX'}$=5.1 Hz, one of 4-H$_2$), 2.75 (1H, H$_A$ of ABXX' system, $J_{AB}$=16.7 Hz, $J_{AX}$=10.0 Hz, $J_{AX'}$=5.3 Hz, one of 4-H$_2$), 4.21 (1H, br s, NH), 4.50 (1H, dd, J=8.9, 3.6 Hz, 2-H), 5.90 (1H, tt, $^2J_{HF}$=53.1 Hz, $^1J_{HF}$=2.9 Hz, CF$_2$H), 6.61 (2H, d, J=7.7 Hz, ArH), 7.04-7.45 (9H, m, ArH).

$^{13}$C-NMR (50.3 MHz, CDCl$_3$): δ 24.6 (3-C), 30.9 (4-C), 55.5 (2-C), 107.7 (CF$_2$H), 113.8 (ArCH), 116.5 (OCF$_2$), 118.1 (quaternary ArC), 118.9 (ArCH), 119.2 (ArCH), 119.8 (ArCH), 120.6 (ArCH), 121.7 (ArCH), 123.1 (CF$_3$), 124.6 (ArCH), 126.9 (ArCH), 127.5 (ArCH), 129.3 (ArCH), 129.9 (ArCH), 140.9 (quaternary ArC), 143.8 (quaternary ArC), 144.6 (quaternary ArC), 147.1 (quaternary ArC), 149.0 (quaternary ArC), 149.2 (quaternary ArC).

Example 15

Asymmetric Reduction of 2-(3-hydroxyphenyl)-5-benzyloxyquinoline

In 40 ml of methanol, 523 mg of 2-(3-hydroxyphenyl)-5-benzyloxyquinoline was dissolved, and 30.4 mg of crystalline (R)-chloro[(1,2,3,4,5-η)-pentamethyl-2,4-cyclopentadien-1-yl](2-pyrrolidinecarboxamidato-κN1, κN2)iridium(III) (Cp*Ir(Cl$^-$)(R-PA-H$^+$)) was added. The mixture was cooled to −20° C. and continuously stirred for 2 days. Then, the reaction was completed. The reaction mixture was concentrated in vacuo and methylene chloride was added. After basification with an aqueous sodium carbonate solution, the resulting layers were separated. The organic layer was washed with water and concentrated. The resulting oil was purified by column chromatography, and the fractions eluted by methylene chloride/n-hexane (4/3) were collected and concentrated in vacuo to give 434 mg of an oil.

This product was identified as 1,2,3,4-tetrahydro-2-(3-hydroxyphenyl)-5-benzyloxyquinoline by NMR. This product was analyzed for optical purity with the use of an optically active column (CHIRALPAC IB; manufactured by Daicel Chemical Industries, Ltd.). As a result, the R-enantiomer was in excess and the optical purity was 78.0% ee.

Specific rotation: $[\alpha]_D^{20}$ 6.5° (c=0.70, CHCl$_3$)

$^1$H-NMR (200 MHz, CDCl$_3$): δ 1.81-2.01 (1H, m, one of 3-H$_2$), 2.04-2.18 (1H, m, one of 3-H$_2$), 2.64-2.93 (2H, m, 4-H$_2$), 4.30 (1H, dd, J=9.2, 3.1 Hz, 2-H), 5.04 (2H, s, OCH$_2$Ph), 6.22 (1H, br d, J=8.1 Hz, ArH), 6.31 (1H, br d, J=8.1 Hz, ArH), 6.72 (1H, ddd, J=8.1, 2.6, 0.9 Hz, ArH), 6.81-6.85 (1H, m, ArH), 6.89-7.00 (2H, m, ArH), 7.14-7.47 (6H, m, ArH).

$^{13}$C-NMR (50.3 MHz, CDCl$_3$): δ 20.4 (3-C), 30.5 (4-C), 55.6 (2-C), 69.7 (benzylic C), 100.9 (ArCH), 107.7 (ArCH), 109.9 (quaternary ArC), 113.4 (ArCH), 114.3 (ArCH), 119.0 (ArCH), 126.9 (ArCH), 127.1 (ArCH), 127.7 (ArCH), 128.4 (ArCH), 129.8 (ArCH), 137.2 (quaternary ArC), 145.8 (quaternary ArC), 146.7 (quaternary ArC), 155.8 (quaternary ArC), 157.0 (quaternary ArC).

Example 16

Asymmetric Reduction of 2-Methylquinoline Using (S)-chloro[(1,2,3,4,5-η)-pentamethyl-2,4-cyclopentadien-1-yl](N-6-quinolinyl-2-pyrrolidinecarboxamidato-κN1, κN2)iridium(III) (Cp*Ir(Cl$^-$)(S-PQA-H$^+$))

In 5 ml of methylene chloride, 36 mg of 2-methylquinoline was dissolved, and 6.0 mg of (S)-chloro[(1,2,3,4,5-η)-pentamethyl-2,4-cyclopentadien-1-yl](N-6-quinolinyl-2-pyrrolidinecarboxamidato-κN1, κN2)iridium(III) (Cp*Ir(Cl$^-$)(S-PQA-H$^+$)) was added. After cooling to −20° C., 1.0 ml of a mixed solvent of formic acid/triethylamine (molar ratio: 5/2) was added, and the mixture was continuously stirred at the same temperature for 48 hours. Then, the reaction was almost completed. This product was analyzed for optical purity with the use of an optically active column (CHIRALCEL OJ-RH; manufactured by Daicel Chemical Industries, Ltd.). As a result, the S-enantiomer was in excess and the optical purity was 91% ee.

Example 17

Asymmetric Reduction of 2-Methylquinoline Using (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) (Cp*Ir(Cl$^-$)(S-PMDBFA-H$^+$))

In 5 ml of methylene chloride, 36 mg of 2-methylquinoline was dissolved, and 7.3 mg of (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) (Cp*Ir(Cl$^-$)(S-PMDBFA-H$^+$)) was added. After cooling to −20° C., 1.0 ml of a mixed solvent of formic acid/triethylamine (molar ratio: 5/2) was added, and the mixture was continuously stirred at the same temperature for 48 hours. Then, the reaction was almost completed. This product was analyzed for optical purity with the use of an optically active column (CHIRALPAC IB; manufactured by Daicel Chemical Industries, Ltd.). As a result, the S-enantiomer was in excess and the optical purity was 92% ee.

Example 18

Synthesis of Cp*Ir(BF$_4^-$)(S-PA-H$^+$)

In 10 ml of methanol, 238 mg of chloro[(1,2,3,4,5-η)-pentamethyl-2,4-cyclopentadien-1-yl] (2-pyrrolidinecarboxamidato-κN1, κN2)iridium(III) (Cp*Ir(Cl$^-$)(S-PA-H$^+$)) was dissolved, and the solution was saturated with argon. To this, 98 mg of silver tetrafluoroborate was added, and the mixture was stirred overnight. The insoluble matter was filtered off, and the filtrate was concentrated in vacuo to give 264 mg of a crystal. The crystal was suspended in a small amount of ethanol, recovered by filtration, washed and dried in vacuo at 50° C. to give 189 mg of a brown crystal.

Elemental analysis: $C_{25}H_{24}BF_4IrN_2O \cdot 2H_2O$ (563.40) calculated value (%) C, 31.98; H, 5.01; N, 4.97 found value (%) C, 32.00; H, 4.86; N, 5.03

$^1$H-NMR (200 MHz, DMSO-d$_6$): δ 1.55-1.84 (3H, m), 1.72 (15H, s, 5Me of Cp*), 1.94-2.10 (1H, m), 2.65-2.85 (1H, m, one of NCH$_2$), 3.40-3.63 (2H, m, one of NCH$_2$ and NCH), 5.57 (1H, br s, CONH), 6.30 (1H, br td-like, NH).

$^{13}$C-NMR (50.3 MHz, DMSO-d$_6$): δ 8.6 (5Me of Cp*), 26.5 (CH$_2$), 29.2 (CH$_2$), 56.4 (NCH$_2$), 62.5 (NCH), 91.8 (ArC of Cp*), 183.0 (C=O).

Example 19

Synthesis of Cp*Ir(PF$_6$)(S-PA-H$^+$)

In 10 ml of methanol, 238 mg of (S)-chloro[(1,2,3,4,5-η)-pentamethyl-2,4-cyclopentadien-1-yl](2-pyrrolidinecarboxamidato-κN1, κN2)iridium(III) (Cp*Ir(Cl$^-$)(S-PA-H$^+$)) was dissolved, and the solution was saturated with argon. To this, 127 mg of silver hexafluorophosphate was added, and the mixture was stirred overnight. The insoluble matter was filtered off, and the filtrate was concentrated in vacuo to give 291 mg of a crystal. The crystal was suspended in a small amount of methanol, recovered by filtration, washed and dried in vacuo at 50° C. to give 177 mg of a light brownish-red crystalline powder.

Elemental analysis: $C_{15}H_{24}F_6IrN_2OP \cdot H_2O$ (603.55) calculated value (%) C, 29.85; H, 4.34; N, 4.64 found value (%) C, 29.96; H, 4.17; N, 4.74

$^1$H-NMR (200 MHz, DMSO-d$_6$): δ 1.54-1.83 (3H, m), 1.72 (15H, s, 5Me of Cp*), 1.95-2.10 (1H, m), 2.65-2.86 (1H, m, one of NCH$_2$), 3.41-3.62 (2H, m, one of NCH$_2$ and NCH), 5.58 (1H, br s, CONH), 6.31 (1H, br td-like, NH).

$^{13}$C-NMR (50.3 MHz, DMSO-d$_6$): δ 8.7 (5Me of Cp*), 26.5 (CH$_2$), 29.2 (CH$_2$), 56.4 (NCH$_2$), 62.5 (NCH), 92.0 (ArC of Cp*), 183.1 (C=O).

Example 20

Synthesis of Cp*Ir(CF$_3$SO$_3^-$)(S-PA-H$^+$)

The reaction of Cp*Ir(Cl$^-$)(S-PA-H$^+$) with silver trifluoromethanesulfonate was conducted in a similar manner as in Example 19 to give a yellow crystalline powder.

$^1$H-NMR (200 MHz, DMSO-d$_6$): δ 1.56-1.84 (3H, m), 1.72 (15H, s, 5Me of Cp*), 1.96-2.10 (1H, m), 2.65-2.86 (1H, m, one of NCH$_2$), 3.41-3.63 (2H, m, one of NCH$_2$ and NCH), 5.58 (1H, br s, CONH), 6.30 (1H, br td-like, NH).

$^{13}$C-NMR (50.3 MHz, DMSO-d$_6$): δ 8.6 (5Me of Cp*), 26.5 (CH$_2$), 29.2 (CH$_2$), 56.4 (NCH$_2$), 62.5 (NCH), 91.9 (ArC of Cp*), 183.0 (C=O).

Example 21

Synthesis of Cp*Ir(SbF$_6^-$)(S-PA-H$^+$)

The reaction of Cp*Ir(Cl$^-$)(S-PA-H$^+$) with silver hexafluoroantimonate was conducted in a similar manner as in Example 19 to give a dark brown crystalline powder.

$^1$H-NMR (200 MHz, DMSO-d$_6$): δ 1.54-1.84 (3H, m), 1.72 (15H, s, 5Me of Cp*), 1.95-2.10 (1H, m), 2.64-2.86 (1H, m, one of NCH$_2$), 3.41-3.62 (2H, m, one of NCH$_2$ and NCH), 5.57 (1H, br s, CONH), 6.30 (1H, br td-like, NH).

$^{13}$C-NMR (50.3 MHz, DMSO-d$_6$): δ 8.6 (5Me of Cp*), 26.5 (CH$_2$), 29.2 (CH$_2$), 56.4 (NCH$_2$), 62.5 (NCH), 91.8 (ArC of Cp*), 183.0 (C=O).

Example 22

Synthesis of Cp*Ir(ClO$_4^-$)(S-PA-H$^+$)

The reaction of Cp*Ir (Cl$^-$)(S-PA-H$^+$) with silver perchlorate was conducted in a similar manner as in Example 19 to give a yellow crystalline powder.

¹H-NMR (200 MHz, DMSO-$d_6$): δ 1.54-1.87 (3H, m), 1.72 (15H, s, 5Me of Cp*), 1.94-2.10 (1H, m), 2.64-2.86 (1H, m, one of $NCH_2$), 3.39-3.62 (2H, m, one of $NCH_2$ and NCH), 5.57 (1H, br s, CONH), 6.30 (1H, br td-like, NH).

¹³C-NMR (50.3 MHz, DMSO-$d_6$): δ 8.6 (5Me of Cp*), 26.5 ($CH_2$), 29.2 ($CH_2$), 56.4 ($NCH_2$), 62.5 (NCH), 91.9 (ArC of Cp*), 183.0 (C=O).

Example 23

Synthesis of Cp*Ir($BF_4^-$)(S-PQA-$H^+$)

To 10 ml of methanol, 302 mg of Cp*Ir (Cl⁻)(S-PQA-$H^+$) was added, and the solution was saturated with argon. To this, 98 mg of silver tetrafluoroborate was added, and the mixture was stirred overnight. Then, 5 ml of water was added, and the mixture was continuously stirred for about 1 hour. The insoluble matter was filtered off, and the filtrate was concentrated in vacuo. The residual concentrate was dissolved in methanol for crystallization. The crystal was collected by filtration, washed and dried in vacuo at 50° C. to give 114 mg of a yellow crystalline powder.

Elemental analysis: $C_{24}H_{29}BF_4IrN_3O.2H_2O$ (690.54) calculated value (%) C, 41.74; H, 4.82; N, 6.09 found value (%) C, 41.44; H, 4.43; N, 6.16

¹H-NMR (200 MHz, DMSO-$d_6$): δ 1.36 (15H, s, 5Me of Cp*), 1.39-1.57 (1H, m), 1.62-2.23 (3H, m), 2.79-3.00 (1H, m, one of $NCH_2$), 3.54-3.78 (2H, m, one of $NCH_2$ and NCH), 6.75 (1H, br td-like, NH), 7.49-7.62 (3H, m, ArH), 7.98 (1H, d, J=8.8 Hz, ArH), 8.29 (1H, dd, J=8.8, 1.2 Hz, ArH), 8.84 (1H, dd, J=4.2, 1.6 Hz, ArH).

¹³C-NMR (50.3 MHz, DMSO-$d_6$): δ 8.4 (5Me of Cp*), 25.7 ($CH_2$), 29.4 ($CH_2$), 55.7 ($NCH_2$), 62.5 (NCH), 89.2 (ArC of Cp*), 121.5 (ArCH), 123.7 (ArCH), 127.9 (quaternary ArC), 128.4 (ArCH), 131.4 (ArCH), 135.3 (ArCH), 145.5 (quaternary ArC), 147.2 (quaternary ArC), 149.6 (ArCH), 182.8 (C=O).

Example 24

Synthesis of Cp*Ir($PF_6^-$)(S-PQA-$H^+$)

The reaction of Cp*Ir(Cl⁻)(S-PQA-$H^+$) with silver hexafluorophosphate was conducted in a similar manner as in Example 23 to give a yellow crystalline powder.

¹H-NMR (200 MHz, DMSO-$d_6$): δ 1.36 (15H, s, 5Me of Cp*), 1.38-1.56 (1H, m), 1.60-2.23 (3H, m), 2.79-3.00 (1H, m, one of $NCH_2$), 3.54-3.78 (2H, m, one of $NCH_2$ and NCH), 6.75 (1H, br td-like, NH), 7.49-7.63 (3H, m, ArH), 7.98 (1H, d, J=8.8 Hz, ArH), 8.29 (1H, dd, J=8.8, 1.2 Hz, ArH), 8.84 (1H, dd, J=4.2, 1.6 Hz, ArH).

¹³C-NMR (50.3 MHz, DMSO-$d_6$): δ 8.4 (5Me of Cp*), 25.7 ($CH_2$), 29.4 ($CH_2$), 55.7 ($NCH_2$), 62.5 (NCH), 89.1 (ArC of Cp*), 121.5 (ArCH), 123.7 (ArCH), 127.9 (quaternary ArC), 128.4 (ArCH), 131.5 (ArCH), 135.3 (ArCH), 145.4 (quaternary ArC), 147.3 (quaternary ArC), 149.6 (ArCH), 182.7 (C=O).

Example 25

Synthesis of Cp*Ir($PF_6^-$)(S-PMDBFA-$H^+$)

To 20 ml of 50% hydrous methanol, 336 mg of Cp*Ir(Cl⁻)(S-PMDBFA-$H^+$) was added, and the solution was saturated with argon. To this, 126 mg of silver hexafluorophosphate was added, and the mixture was stirred overnight. The reaction mixture was heated to about 50° C. and stirred for about 30 minutes, the insoluble matter was filtered off, and the filtrate was concentrated in vacuo. The concentrated residue was dissolved in 50% hydrous methanol for crystallization. The crystal was collected by filtration, washed and dried in vacuo at 50° C. to give 190 mg of a reddish-brown crystalline powder.

Elemental analysis: $C_{28}H_{32}F_6IrN_2O_3P$ (781.73) calculated value (%) C, 43.02; H, 4.13; N, 3.58 found value (%) C, 43.14; H, 4.36; N, 3.91

¹H-NMR (200 MHz, DMSO-$d_6$, mainly two rotamers observed in the ratio ca. 7:3): δ 1.31 (15H×0.7, s, 5Me of Cp* for the major), 1.58-2.18 (4H, m), 1.34 (15H×0.3, s, 5Me of Cp* for the minor), 2.83-3.12 (1H, m, one of $NCH_2$), 3.50-3.76 (2H, m, one of $NCH_2$ and NCH), 3.84 (3H×0.7, s, OMe for the major), 3.88 (3H×0.3, s, OMe for the minor), 6.89 (0.7H, br td-like, NH for the major), 7.04 (0.3H, br td-like, NH for the minor), 7.31-7.54 (2H, m, ArH), 7.38 (0.3H, s, ArH), 7.39 (0.7H, s, ArH), 7.65 (1H, br d, J=7.5 Hz, ArH), 7.77 (0.7H, s, ArH), 7.81 (0.3H, s, ArH), 8.12 (1H, dd, J=7.5, 1.1 Hz, ArH).

¹³C-NMR (50.3 MHz, DMSO-$d_6$, two rotamers observed): δ 8.2 (5Me of Cp* for the major), 8.3 (5Me of Cp* for the minor), 25.4 ($CH_2$ for the major), 25.7 ($CH_2$ for the minor), 29.1 ($CH_2$ for the major), 29.2 ($CH_2$ for the minor), 54.8 ($CH_2$ for the minor), 55.2 ($CH_2$ for the major), 55.4 (OMe for the minor), 56.2 (OMe for the major), 61.7 (NCH), 87.0 (quaternary ArC of Cp* for the major), 88.6 (quaternary ArC of Cp* for the minor), 95.0 (ArC), 102.3 (ArCH for the minor), 102.7 (ArCH for the major), 109.9 (ArCH), 111.5 (ArCH for the major), 112.0 (ArCH for the minor), 120.4 (ArCH for the minor), 120.8 (ArCH for the major), 122.8 (ArCH), 124.1 (quaternary ArC), 126.7 (ArCH), 137.7 (quaternary ArC for the minor), 139.1 (quaternary ArC for the major), 149.4 (quaternary ArC for the minor), 149.6 (quaternary ArC for the major), 151.0 (quaternary ArC for the minor), 151.8 (quaternary ArC for the major), 156.0 (quaternary ArC for the major), 156.1 (quaternary ArC for the minor), 183.7 (CO for the major), 184.8 (CO for the minor).

Example 26

Asymmetric Reduction of 2-Methylquinoline Using Cp*Ir($PF_6^-$)(S-PA-$H^+$)

In 5 ml of methylene chloride, 36 mg of 2-methylquinoline was dissolved, and 6.8 mg of Cp*Ir($PF_6^-$)(S-PA-$H^+$) was added. After cooling to −20° C., 1.0 ml of a mixed solvent of formic acid/triethylamine (molar ratio: 5/2) was added, and the mixture was continuously stirred at the same temperature for 48 hours. Then, the reaction was completed. This product was analyzed for optical purity with the use of an optically active column (CHIRALCEL OJ-RH; manufactured by Daicel Chemical Industries, Ltd.). As a result, the S-enantiomer was in excess and the optical purity was 82% ee.

Example 27

Asymmetric Reduction of 2-Methylquinoline Using Cp*Ir($CF_3SO_3^-$)(S-PA-$H^+$)

In 5 ml of methylene chloride, 36 mg of 2-methylquinoline was dissolved, and 5.9 mg of Cp*Ir($CF_3SO_3^-$)(S-PA-$H^+$) was added. After cooling to −20° C., 1.0 ml of a mixed solvent of formic acid/triethylamine (molar ratio: 5/2) was added, and the mixture was continuously stirred at the same temperature for 48 hours. Then, the reaction was completed. This product was analyzed for optical purity with the use of an optically active column (CHIRALCEL OJ-RH; manufactured by Daicel Chemical Industries, Ltd.). As a result, the S-enantiomer was in excess and the optical purity was 86% ee.

Example 28

Asymmetric Reduction of 2-Methylquinoline Using Cp*Ir(BF$_4^-$)(S-PQA-H$^+$)

In 5 ml of methylene chloride, 36 mg of 2-methylquinoline was dissolved, and 6.6 mg of Cp*Ir(BF$_4^-$)(S-PQA-H$^+$) was added. After cooling to −20° C., 1.0 ml of a mixed solvent of formic acid/triethylamine (molar ratio: 5/2) was added, and the mixture was continuously stirred at the same temperature for 48 hours. Then, the reaction was almost completed. This product was analyzed for optical purity with the use of an optically active column (CHIRALCEL OJ-RH; manufactured by Daicel Chemical Industries, Ltd.). As a result, the S-enantiomer was in excess and the optical purity was 91% ee.

INDUSTRIAL APPLICABILITY

The production method of the present invention enables low-cost production of optically active 2-substituted-1,2,3,4-tetrahydroquinolines using simple equipment under simple process control and therefore is industrially useful.

The invention claimed is:

1. A method for producing optically active 2-substituted-1,2,3,4-tetrahydroquinolines, comprising reducing a quinoline compound represented by formula [I]:

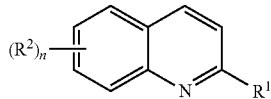

[I]

wherein R$^1$ represents an optionally substituted alkyl group, an optionally substituted aryl group, an optionally substituted aralkyl group, an optionally substituted cycloalkyl group or an optionally substituted heteroaryl group, R$^2$ represents a hydrogen atom, an optionally substituted alkyl group, an optionally substituted aryl group, an optionally substituted aralkyl group, an optionally substituted cycloalkyl group, an optionally substituted heteroaryl group, an optionally substituted hydroxyl group, an optionally substituted thiol group, an optionally substituted amino group, an optionally substituted carbamoyl group, an optionally substituted aryloxy group, an optionally substituted heteroaryloxy group, a carboxyl group, an esterified carboxyl group, a cyano group, a nitro group or a halogen atom, R$^2$ is bound to the quinoline ring at any one of positions 5 to 8, n is an integer of 1 to 4, and when n is not less than 2, R$^2$ groups adjacent to each other may join together to form a ring, in the presence of a hydrogen donor compound and an iridium(III) complex having a chiral prolinamide compound as a ligand to give an optically active 2-substituted-1,2,3,4-tetrahydroquinoline represented by formula [II]:

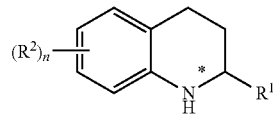

[II]

(wherein R$^1$, R$^2$ and n are as defined in formula [I], and the symbol "*" indicates that the carbon atom is a chiral center), wherein the iridium(III) complex having a chiral prolinamide compound as a ligand is represented by formula [IV]:

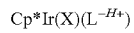

Cp*Ir(X)(L$^{-H+}$) [IV]

wherein X represents Cl$^-$, p-CH$_3$C$_6$H$_4$SO$_3^-$, CH$_3$SO$_3^-$, CF$_3$SO$_3^-$, NO$_3^-$, BF$_4^-$, ClO$_4^-$, PF$_6^-$, SbF$_6^-$, B[3,5-di(trifluoromethyl)phenyl]$_4^-$ or B(4-fluorophenyl)$_4^-$, L is a compound represented by formula [III]:

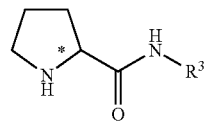

[III]

wherein R$^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center), and Cp* represents (1,2,3,4,5-η)-pentamethyl-2,4-cyclopentadien-1-yl, wherein the hydrogen donor compound is formic acid, ammonium formate, sodium formate, potassium formate or 2-propanol, wherein the iridium(III) complex is isolated and purified by crystallization.

2. The method according to claim 1, wherein the chiral prolinamide compound is a compound represented by formula [III]:

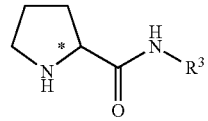

[III]

(wherein R$^3$ represents a hydrogen atom, an optionally substituted alkyl group, an optionally substituted aryl group, an optionally substituted aralkyl group, an optionally substituted cycloalkyl group or an optionally substituted heteroaryl group, and the symbol "*" indicates that the carbon atom is a chiral center).

3. The method according to claim 1, wherein the chiral prolinamide compound is (R)-proline heteroaryl amide or (S)-proline heteroaryl amide.

4. The method according to claim 1, wherein the chiral prolinamide compound is (R)—N-(6-quinolinyl)-2-pyrrolidinecarboxamide or (S)—N-(6-quinolinyl)-2-pyrrolidinecarboxamide.

5. The method according to claim 1, wherein the chiral prolinamide compound is (R)—N-(2-methoxy-3-dibenzofuranyl)-2-pyrrolidinecarboxamide or (S)—N-(2-methoxy-3-dibenzofuranyl)-2-pyrrolidinecarboxamide.

6. The method according to claim 1, wherein the chiral prolinamide compound is (R)-2-pyrrolidinecarboxamide or (S)-2-pyrrolidinecarboxamide.

7. The method according to claim 1, wherein the complex has a ligand of formula [III] in which $R^3$ is hydrogen, a 6-quinolinyl group or a 2-methoxy-3-dibenzofuranyl group.

8. The method according to claim 1, wherein the iridium (III) complex having a chiral prolinamide compound as a ligand is an (R)- or (S)-chloro[(1,2,3,4,5-η)-pentamethyl-2,4-cyclopentadien-1-yl][N-(2-methoxy-3-dibenzofuranyl)-2-pyrrolidinecarboxamidato-κN1, κN2]iridium(III) catalyst, or an (R)- or (S)-chloro[(1,2,3,4,5-η)-pentamethyl-2,4-cyclopentadien-1-yl](N-6-quinolinyl-2-pyrrolidinecarboxamidato-κN1, κN2)iridium(III) catalyst.

9. The method according to claim 1, wherein the iridium (III) complex having a chiral prolinamide compound as a ligand is an (R)- or (S)-chloro[(1,2,3,4,5-η)-pentamethyl-2,4-cyclopentadien-1-yl](2-pyrrolidinecarboxamidato-κN1, κN2)iridium(III) catalyst.

10. The method according to claim 1, wherein the iridium (III) complex having a chiral prolinamide compound as a ligand is crystalline.

11. The method according to claim 1, wherein the iridium (III) complex having a chiral prolinamide compound as a ligand is amorphous.

12. The method according to claim 1, wherein the hydrogen donor compound is formic acid.

* * * * *